(12) United States Patent
Fasano et al.

(10) Patent No.: US 7,622,264 B2
(45) Date of Patent: Nov. 24, 2009

(54) METHODS FOR SCREENING FOR MODULATORS OF CXCR3 SIGNALING

(75) Inventors: Alessio Fasano, West Friendship, MD (US); Ruiliang Lu, Baltimore, MD (US); Stefanie N. Vogel, Columbia, MD (US); Julie Brownley, Towson, MD (US); Karen Lammers, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 69 days.

(21) Appl. No.: 11/354,948

(22) Filed: Feb. 16, 2006

(65) Prior Publication Data

US 2007/0048801 A1 Mar. 1, 2007

Related U.S. Application Data

(60) Provisional application No. 60/653,118, filed on Feb. 16, 2005, provisional application No. 60/741,998, filed on Dec. 2, 2005.

(51) Int. Cl.
G01N 33/53 (2006.01)
G01N 33/566 (2006.01)
C07K 14/705 (2006.01)

(52) U.S. Cl. ............................. 435/7.1; 435/7.2; 435/4; 530/350

(58) Field of Classification Search ........................ None
See application file for complete search history.

(56) References Cited

U.S. PATENT DOCUMENTS

| | | | |
|---|---|---|---|
| 6,794,379 | B2 | 9/2004 | Medina et al. |
| 7,157,418 | B1 | 1/2007 | McDonald et al. |
| 2002/0169159 | A1 | 11/2002 | Medina et al. |
| 2003/0017979 | A1 | 1/2003 | Mack et al. |
| 2003/0055054 | A1 | 3/2003 | Medina et al. |
| 2003/0069234 | A1 | 4/2003 | Medina et al. |
| 2004/0235823 | A1 | 11/2004 | Bridger et al. |
| 2004/0242498 | A1 | 12/2004 | Collins et al. |
| 2005/0070573 | A1 | 3/2005 | Lin et al. |
| 2005/0075333 | A1 | 4/2005 | Medina et al. |
| 2005/0113414 | A1 | 5/2005 | Watson et al. |
| 2005/0191702 | A1 | 9/2005 | Mack et al. |
| 2006/0036093 | A1 | 2/2006 | Lin et al. |
| 2006/0069099 | A1 | 3/2006 | Fu et al. |
| 2006/0069106 | A1 | 3/2006 | Fu et al. |
| 2006/0069127 | A1 | 3/2006 | Fu et al. |
| 2006/0217392 | A1 | 9/2006 | Anilkumar et al. |
| 2006/0276448 | A1 | 12/2006 | Zeng et al. |
| 2006/0276457 | A1 | 12/2006 | Yu et al. |
| 2006/0276479 | A1 | 12/2006 | Kim et al. |
| 2006/0276480 | A1 | 12/2006 | Wong et al. |
| 2007/0015773 | A1 | 1/2007 | Bergeron et al. |
| 2007/0021611 | A1 | 1/2007 | McGuinness et al. |
| 2007/0048801 | A1 | 3/2007 | Fasano et al. |
| 2007/0054919 | A1 | 3/2007 | Rosenblum et al. |

FOREIGN PATENT DOCUMENTS

| | | |
|---|---|---|
| EP | 1098664 | 5/2001 |
| EP | 1163238 | 12/2001 |
| WO | WO-0004926 | 2/2000 |
| WO | WO-0056729 | 9/2000 |
| WO | WO-02069961 | 9/2002 |
| WO | WO-02083143 | 10/2002 |
| WO | WO-02096397 | 12/2002 |
| WO | WO-2004075863 | 9/2004 |
| WO | WO-2004083394 | 9/2004 |
| WO | WO-2005058815 | 6/2005 |
| WO | WO-2006004915 | 1/2006 |
| WO | WO-2006004924 | 1/2006 |
| WO | WO-2006004925 | 1/2006 |
| WO | WO-2006023381 | 3/2006 |
| WO | WO-2006052723 | 5/2006 |
| WO | WO-2006084173 | 8/2006 |
| WO | WO-2006088836 | 8/2006 |
| WO | WO-2006088837 | 8/2006 |
| WO | WO-2006088840 | 8/2006 |
| WO | WO-2006088919 | 8/2006 |
| WO | WO-2006088920 | 8/2006 |
| WO | WO-2006088921 | 8/2006 |
| WO | WO-2006091428 | 8/2006 |
| WO | WO-2006112925 | 10/2006 |
| WO | WO-2006129679 | 10/2006 |
| WO | WO-2007002701 | 1/2007 |
| WO | WO-2007002742 | 1/2007 |
| WO | WO-2007024715 | 3/2007 |

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Skolnick et al. (2000). From genes to protein structure and function: novel applications of computational approaches in the genomic era. Trends in Biotechnology. 18:34-39.*
Hajduk, P. J., et al. Quarterly Reviews of Biophysics, 1999. 32 (3): 211-40.

(Continued)

Primary Examiner—Christine J Saoud
Assistant Examiner—Jon M Lockard
(74) Attorney, Agent, or Firm—Morgan, Lewis & Bockius LLP

(57) ABSTRACT

CXCR3 is identified as a physiological receptor for Gliadin. Assays for determining modulators of CXCR3 signaling are provided. Fragments of gliadin which function as inhibitors of CXCR3 signaling can be determined. Methods for treating diseases relating to gluten and/or autoimmunity by targeting CXCR3 are provided. Such diseases include celiac disease, gluten sensitivity, gluten allergy, rheumatoid arthritis, multiple sclerosis, immune-mediated or type 1 diabetes mellitus, inflammatory bowel diseases, systemic lupus erythematosus, psoriasis, scleroderma, and autoimmune thyroid diseases.

17 Claims, 11 Drawing Sheets

OTHER PUBLICATIONS

Annunziato et al., Assessment of Chemokine Receptor Expression by Human TH1 and TH2 Cells in Vitro and in Vivo, Journal of Leukocyte Biology, May 1999, Vol. 65, pp. 691-699.

Autschbach et al., Expression of Chemokine Receptors in Normal and Inflamed Human Intestine, Tonsil, and Liver—Am Immunohistochemical Analysis with New Monoclonal Antibodies from the 8th International Workshop and Conference on Human Leucocyte Differentiation Antigens, Cellular Immunology, 2005, pp. 110-114.

Berrebi et al., Cytokines, Chemokine Receptors, and Homing Molecule Distribution in the Rectum and Stomach of Pediatric Patients with Ulcerative Colitis, Journal of Pediatric Gastroenterology and Nutrition, Sep. 2003, pp. 300-308.

Biswas et al., In vivo Modulation of Leukocyte Trafficking Receptor Following Therapeutic Purging of Myeloid Cells: Implications for Treatment of HIV Infection and Other Immune Disorders, Clinical Immunology, 2003, pp. 355-358.

Brescia et al., Novel Small-Molecule Antagonists of the Chemokine Receptor CCR3, Poster Session, Aug. 28, 2005, 1 page.

Brooklyn et al., Chemokine Receptor CXCR3 Expression by Lamina Propria T Cells in Chrohns Disease, Digestive Disease Week Abstracts and Itinerary Planner, 2003, 3 pages.

Brownley et al., Role of CXCR3 in Gliadin-Mediated Zonulin Release and Increased Intestinal Permeability, Gastroenterology, Apr. 2006, 3 pages.

Ghosh et al., Interfering with Interferons in Inflammatory Bowel Disease, Gut, 2006; 55, pp. 1071-1073.

Gomariz et al., VIP-PACAP System in Immunity New Insights for Multitarget Therapy, Annuals New York Academy of Sciences, 2005, 1070, pp. 51-74.

Barbara A. Hendrickson, Gastric Inflammation as a Feature of Ulcerative Colitis, Journal of Pediatric Gastroenterology and Nutrition, Sep. 2003, 37, pp. 228-229.

Hyun et al., IP-10 Plays a Critical Role in TM-Mediated Colitis: Its Role in Immune Cell Recruitment to the MLN and Colon, Digestive Disease Week Abstracts and Itinerary Planner, 2003, 3 pages.

Imamura et al., Involvement of Th1 Cells and Heat Shock Protein 60 in the Pathogenesis of Intestinal Behçet's Disease, Clinical and Experimental Immunology, 2005, pp. 371-378.

Inatomi et al., Butyrate Blocks Interferon-γ-Inducible Protein-10 Release in Human Intestinal Subepithelial Myofibrolasts, Journal of Gastroenterology, 2005, pp. 40:483-489.

Jo et al., CCR4 Is an Up-Reglated Chemokine Receptor of Peripheral Blood Memory CD4$^+$ T Cells in Crohn's Disease, Clin Exp Immunol 2003; pp. 132:332-338.

Johnson et al., Expression of CXCR3, CXCR4, CCR5 in Early and Late Pediatric Crohn's Disease Intestinal Mucosal T-Lymphocytes, Digestive Disease Week Abstracts and Itinerary Planner, 2003, 3 pages.

Kitamura et al., Pivotal Roles of Interleukin-6 in Transmural Inflammation in Marine T Cell Transfer Colitis, Gastroenterology, Apr. 2006, 3 pages.

Kouroumalis et al., The Chemokines CXCL9, CXCL10, and CXCL11 Differentially Stimulate Gαi-Independent Signaling and Actin Responses in Human Intestinal Myofibroblasts[1], The American Association of Immunologists, Inc., 2005, pp. 5403-5411.

Kristensen et al., CXC Chemokine Receptor 3 Expression Increases the Disease-inducing Potential of CD4$^+$ CD25$^-$ T Cells in Adoptive Transfer Colitis, Inflamm Bowel Dis, May 5, 2006, vol. 12, pp. 374-381.

Kristensen et al., Chemokines Involved in Protection from Colitis by CD4$^+$ CD25$^+$ Regulatory T Cells, Inflamm Bowel Dis, Jul. 7, 2006, vol. 12, No. 7, pp. 612-618.

Liu et al., Severe Disease, Unaltered Leukocyte Migration, and Reduced IFN-γ Production in CXCR3-/- Mice with Experimental Autoimmune Encephalomyelitis[1], The Journal of Immunology, 2006, pp. 4399-4409.

Medina et al., Optimization and Biological Profile of 2,3-Substituted Quinazolin-4-Ones as Potent CXCR3 Antagonists, Emerging Therapies for the Prevention of Solid Organ Transplant Rejection, Mar. 28, 2006, 1 page.

Oki et al., Accumulation of CCR5+ T Cells Around RANTES+ Granulomas in Crohn's Disease: A Pivotal Site of Th1-Shifted Immune Response?, Laboratory Investigation 2005, 85, pp. 137-145.

Papadakis et al., Expression and Regulation of the Chemokine Receptor CXCR3 on Lymphocytes from Normal and Inflammatory Bowel Disease Mucosa, Inflamm Bowel Dis, Nov. 2004, vol. 10, No. 6, pp. 778-788.

Sakuraba et al., Phenotypic and Functional Analysis of Dendritic Cells Isolated from the Mesenteris Lymph Nodes of Human Inflammatory Bowel Disease, Digestive Disease Week Abstracts and Itinerary Planner, 2003, 3 pages.

Saniabadi et al., Adacolumn for Selective Leukocytapheresis as a Non-Pharmacological Treatment for Patients with Disorders of the Immune System: An Adjunct or an Alternative to Drug Therapy?, Journal of Clinical Apheresis 20, 2005, pp. 171-185.

Saniabadi et al., Selective Mycloid Leukocyte Purging as a Non-Pharmacological Treatment for Patients with Inflammatory Bowel Disease: A Report on Changes in Pro- and Anti-Inflammatory Factors, Gastroenterology, Apr. 2005, 3 pages.

Sasaki et al., Blockade of CXCL10 Protects Mice from Acute Colitis and Enhances Crypt Cell Survival, Eur. J. Immunol, 2002, 32, pp. 3197-3205.

Singh et al., Colitis in IL-10-/- Mice is Mediated in Part by CXCL10 Production by CD4$^+$T Cells, Neutophils, and NKL Cells as Well as CXCR3+ Dendritic Cells, FASEB Journal, Mar. 4, 2005, 3 pages.

Singh et al., IFN-γ- Inducible Chemokines Enhance Adaptive Immunity and Colitis, Journal of Interferon and Cytokine Research, 2003, pp. 591-600.

Singh et al., Inhibition of IFN-γ- Inducible Protein-10 Abrogates Colitis in IL-10$^{-/-}$ Mice[1], The Journal of Immunology, 2003, pp. 1401-1406.

Smit et al., CXCR3-Mediated Chemotaxis of Human T Cells is Regulated by a $G_1$ and Phospholipase C-Dependent Pathway and Not Via Activation of MEK/p44/p42 MAPK nor Akt/PI-3 Kinase, Chemokines, Sep. 15, 2003, pp. 1959-1965.

Sui et al., Neuronal Apoptosis is mediated by CXCL10 Overexpression in Simian Human Immunodeficiency Virus Encephalitis, American Journal of Pathology, vol. 164, No. 5, May 5, 2004, pp. 2668-2677.

Suzuki et al., Blockade of Interferon-Gamma-Inducible Protein 10 Ameliorates Chronic Experimental Colitis Through Blocking Cellular Trafficking and Protecting Intestinal Epithelial Cells, Digestive Disease Week Abstracts and Itinerary Planner, 2003, 3 pages.

Suzuki et al., Amelioration of Acute Colitis of Mice by Enema of nti-Interferon-Inducible-Protein 10-Antibody, Gastroenterology, Apr. 2004, 3 pages.

Tokuyama et al., The Simultaneous Blockade of Chemokine Receptors CCR2, CCR5 and CXCR3 by a Non-Peptide Chemokine Receptor Antagonist Protects Mice from Dextran Sodium Sulfate-Mediated Colitis, International Immunology, May 12, 2005, vol. 17, No. 8, pp. 1023-1034.

Yu et al., Phenotypie and Functional Characterization of CCR9+ T Lymphocytes in Small Intestinal Crohn's Disease (CD), Gastroenterology, Apr. 2006, 3 pages.

Yuan et al., Chemokine Receptor CXCR3 Expression in Inflammatory Bowel Disease, Inflammatory Bowel Diseases, 2001, pp. 281-286.

Zhang et al., Visilizumab Treatment Promotes Morphological Recovery, Reduces inflammatory Markers and Affects T Cell Subsets in Mucosa of Ulcerative Colitis Patients, Apr. 2006, 3 pages.

Tularik Inc., Tularik Initiates Phase 2 Clinical Trial of T487 in Psoriasis, Press Release, Dec. 10, 2003, 2 pages.

Author Unknown, Into Immunology, BioVenture View, 1997, vol. 12, No. 3, 10 pages.

Tularik Inc., Tularik Announces 2003 Third Quarter Financial Results, Press Release, Oct. 16, 2003, 4 pages.

Chemocentryx, ChemoCentryx Initiates Phase II Clinical Trial of Traficet-EN™ in Inflammatory Bowel Disease, Press Release, Jan. 6, 2005, 3 pages.

Chemocentryx, ChemoCentryx Releases $33 Million in Private Financing, Press Release, Jun. 17, 2004, 3 pages.

* cited by examiner

Wild Type mice experiments: Gluten Challenge

Zonulin

TEER

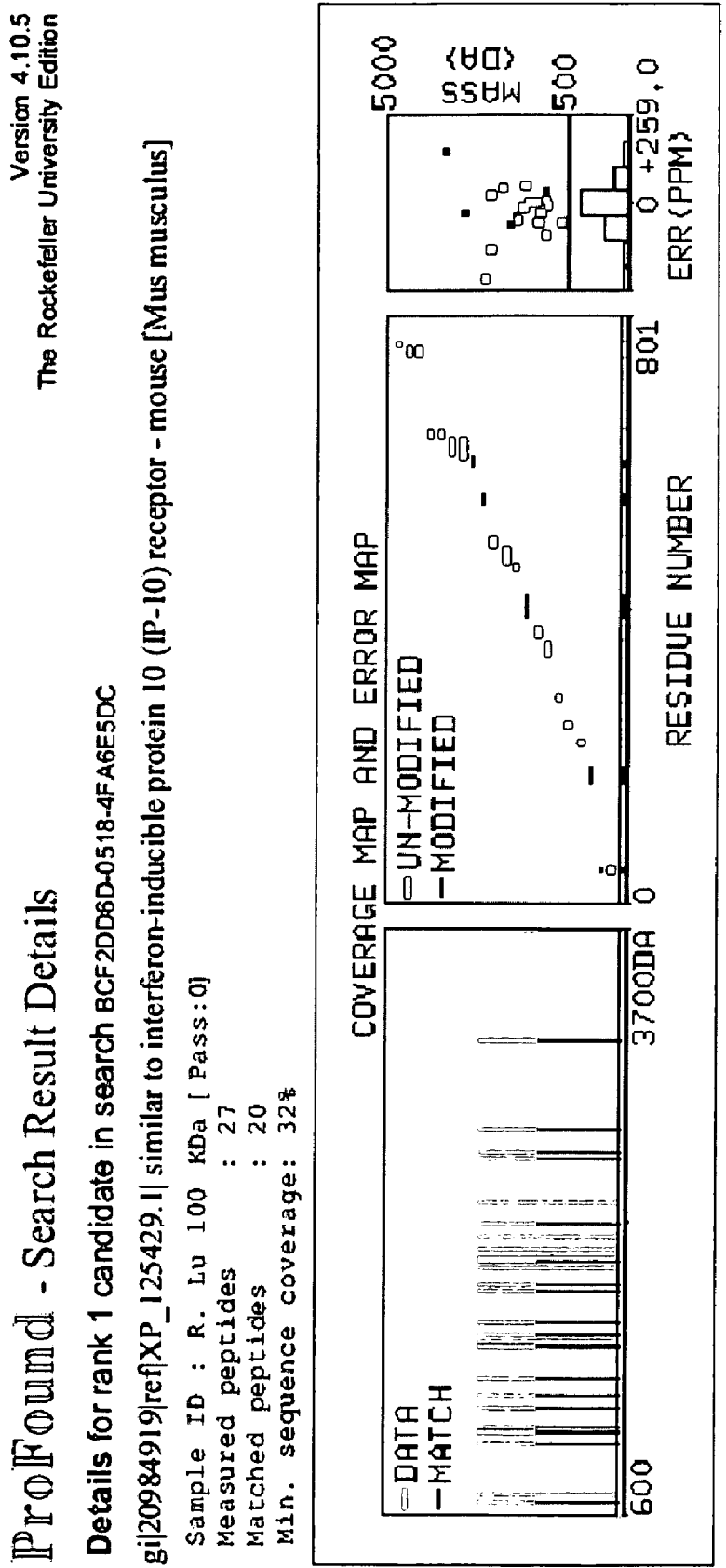

Figure 9
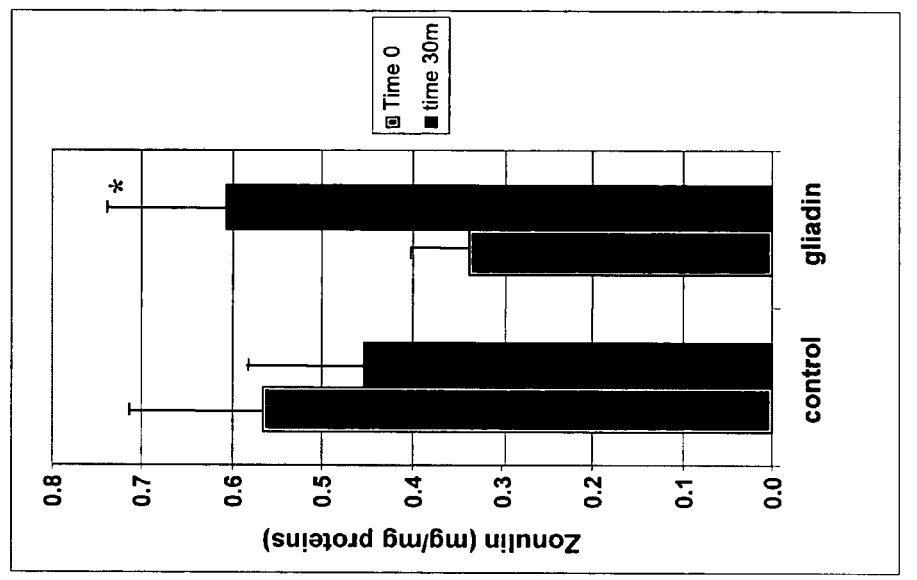
Fig. 9B
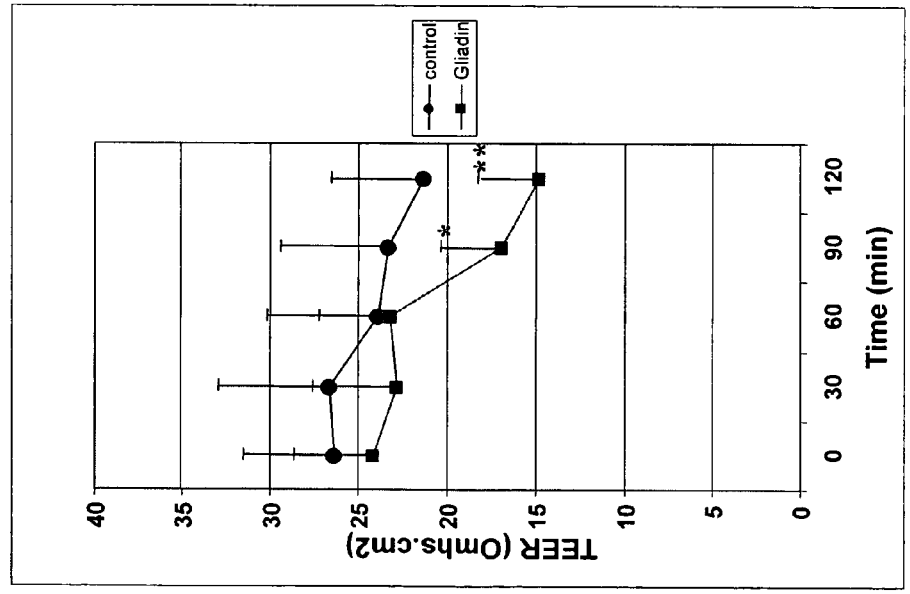
Fig. 9A
*p<0.05
**p<0.02

US 7,622,264 B2

METHODS FOR SCREENING FOR MODULATORS OF CXCR3 SIGNALING

CROSS REFERENCE TO RELATED APPLICATIONS

This application claims priority to U.S. provisional patent application Ser. No. 60/653,118, filed Feb. 16, 2005, and to U.S. provisional patent application Ser. No. 60/741,998, filed Dec. 2, 2005, the contents of both of which are specifically incorporated herein by reference.

STATEMENT REGARDING FEDERALLY SPONSORED RESEARCH

The subject matter of this application was in part funded by the National Institutes of Health grant no. A118797. The United States Governments has certain rights in the invention.

TECHNICAL FIELD OF THE INVENTION

This invention is related to the area of autoimmune diseases. In particular, it relates to treatment and drug screening and discovery for autoimmune diseases.

BACKGROUND OF THE INVENTION

Environmental stimuli, such as microorganisms and gluten, induce zonulin release in the intestine, brain, heart, and other organs. Zonulin release causes an increase in permeability of epithelia as measured by a decrease in trans-epithelial electrical resistance (TEER) (ex vivo) or the Lactulose/mannitol test (in vivo). Presumably, the environmental stimuli interact with the surface of cells, possibly by binding to a receptor on the cell surface. However, such a receptor has not been identified.

Many inflammatory diseases are thought to be autoimmune. These include rheumatoid arthritis, multiple sclerosis, immune-mediated or type 1 diabetes mellitus, inflammatory bowel diseases, systemic lupus erythematosus, psoriasis, scleroderma, and autoimmune thyroid diseases. Prolonged inflammation is often associated with these diseases, although the inflammation is thought to be a sequela rather than a primary pathological insult.

Chemokine (C-X-C motif) receptor 3 (CXCR3) is a G protein-coupled receptor which is known to bind to three chemokines, IP10 (interferon-γ-inducible 10 kDa protein), MIG (monokine induced by interferon-γ) and I-TAC (interferon-inducible T cell α-chemoattractant). IP10, MIG and I-TAC are termed CXC chemokines, because they contain a CXC sequence motif. CXCR3 has been linked to integrin activation, cytoskeletal changes, and chemotaxis. CXCR3 is prominently expressed in inflamed tissues.

There is a continuing need in the art for methods to treat autoimmune diseases more effectively and to discover or identify drugs which are suitable for treating autoimmune diseases.

SUMMARY OF THE INVENTION

One embodiment of the invention provides a method to screen for modulators of CXCR3 signaling. Gliadin or a fragment of gliadin (e.g. a fragment comprising at least six amino acid residues) is contacted with CXCR3. Binding of the gliadin or fragment of gliadin to CXCR3 is determined. A fragment of gliadin which binds to CXCR3 is identified as a modulator of CXCR3 signaling.

Another embodiment of the invention provides a method to screen for modulators of CXCR3 signaling. Gliadin or a fragment of gliadin comprising at least six amino acid residues is contacted with a first cell which expresses CXCR3 and with a second cell which does not express CXCR3. Binding of the gliadin or fragment to the first and second cells is determined. A fragment of gliadin which binds preferentially to the first cell relative to the second cell is identified as a modulator of CXCR3 signaling.

Still another embodiment of the invention provides a method to screen for modulators of CXCR3 signaling. Gliadin or fragment of gliadin comprising at least six amino acid residues is contacted with CXCR3 or another CXCR3 ligand, such as IP10, MIG, or ITAC. Inhibition of binding of ligand to CXCR3 caused by the fragment of gliadin is determined. A fragment of gliadin which inhibits binding of ligand to CXCR3 is identified as a modulator of CXCR3 signaling.

Yet another aspect of the invention is a method to screen for modulators of CXCR3 signaling. A fragment of gliadin comprising at least six amino acid residues is contacted with a cell which expresses CXCR3 or another CXCR3 ligand, such as IP10, MIG, or ITAC. Binding of ligand to the cell is determined. A fragment of gliadin which inhibits binding of ligand to the cell is identified as a modulator of CXCR3 signaling.

Also provided by the present invention is a method to screen for modulators of zonulin release. A test compound is contacted with CXCR3. Binding of the test compound to CXCR3 is determined. A test compound which binds to CXCR3 is identified as a modulator of zonulin release.

Another embodiment provided by the present invention is a method to screen for modulators of zonulin release. A test compound is contacted with CXCR3. Binding of the gliadin to CXCR3 in the presence and absence of the test compound is determined. A test compound which inhibits binding of gliadin to CXCR3 is identified as a modulator of zonulin release.

Still another embodiment of the invention is a method to screen for modulators of zonulin release. A test compound is contacted with a first cell which expresses CXCR3 and with a second cell which does not express CXCR3. Binding of the test compound to the first and second cells is determined. A test compound which binds preferentially to the first cell relative to the second cell is identified as a modulator of zonulin release.

Even a further embodiment is a method to screen for modulators of zonulin release. A test compound is contacted with a cell which expresses CXCR3 . Binding of gliadin to the cell is determined. A test compound which inhibits binding of gliadin to the cell is identified as a modulator of zonulin release.

Another embodiment of the invention is a method of treating a patient with a disease selected from the group consisting of celiac disease, gluten allergy, gluten sensitivity, and gluten ataxia. An antibody which specifically binds to CXCR3 is administered to the patient. Zonulin release is thereby inhibited.

A further embodiment of the invention is a method of treating a patient with an autoimmune or inflammation-associated disease. Typically, these diseases will be characterized by an undesired CXCR3 signaling. The disease is selected from the group consisting of type 1 diabetes, celiac disease, autoimmune hepatitis, multiple sclerosis, autism, dermatitis herpetiformis, IgA nephropathy, primary biliary cirrhosis, rheumatoid arthritis, systemic lupus erythematosus, Grave's disease, Hashimoto's disease, and depression. An antibody which specifically binds to CXCR3 is administered to the patient. CXCR3 signaling is thereby inhibited.

In some embodiments, the present invention provides methods of identifying a CXCR3 ligand comprising contacting a cell expressing CXCR3 with gliadin or a fragment thereof and a compound to be tested and determining the amount of gliadin or fragment thereof bound to the cell. For example, one or more gliadins or fragments thereof may be labeled with one or more fluorescent moieties. A CXCR3-expressing cell may then be brought into contact with the fluorescently labeled gliadin or fragment in the presence of the compound to be tested. The binding of the gliadin or fragment thereof and CXCR3 may be determined using standard techniques. Suitable techniques include, but are not limited to, fluorescence activated cell sorting (FACS), fluorescent microscopy, and fluorescence spectrophotometry. Optionally the gliadin or fragment thereof may be contacted with CXCR3-expressing cells in the absence of compound to be tested and the amount of binding of gliadin or fragment thereof to CXCR3-expressing cell may be determined. The amount of binding in the presence of compound to be tested and in the absence of compound to be tested may be compared. Other techniques known to those skilled in the art may be used to quantify the gliadin or fragment thereof binding. For example, cells expressing CXCR3 may be fixed to a solid surface, for example, a microtiter plate or a bead (e.g., a magnetic bead) and contacted with fluorescently labeled gliadin or fragment thereof. The amount of bound fluorescently labeled gliadin may be determined. In some embodiments, gliadin may be labeled with a detectable moiety other than a fluorescent moiety, for example, with biotin or digoxigenein and, detected with a suitable reagent, for example, streptavidin or anti-digoxigenin antibody.

In some embodiments, the present invention provides methods of identifying a CXCR3 ligand comprising contacting a purified CXCR3 or fragment thereof with gliadin or a fragment thereof and a compound to be tested and determining the amount of gliadin or fragment thereof bound to the CXCR3. For example, one or more gliadins or fragments thereof may be labeled with one or more fluorescent moieties. CXCR3 may then be brought into contact with the fluorescently labeled gliadin or fragment in the presence of the compound to be tested. The binding of the gliadin or fragment thereof and CXCR3 may be determined using standard techniques. Suitable techniques include, but are not limited to, ELISA and fluorescence spectrophotometry. Optionally the gliadin or fragment thereof may be contacted with CXCR3 in the absence of compound to be tested and the amount of binding of gliadin or fragment thereof to CXCR3 cell may be determined. The amount of binding in the presence of compound to be tested and in the absence of compound to be tested may be compared. Other techniques known to those skilled in the art may be used to quantify the gliadin or fragment thereof binding. For example, CXCR3 may be fixed to a solid surface, for example, a microtiter plate or a bead (e.g., a magnetic bead) and contacted with fluorescently labeled gliadin or fragment thereof. The amount of bound fluorescently labeled gliadin may be determined. In some embodiments, gliadin may be labeled with a detectable moiety other than a fluorescent moiety, for example, with biotin or digoxigenein and, detected with a suitable reagent, for example, streptavidin or anti-digoxigenin antibody. In some embodiments, gliadin or fragment thereof may be attached to a solid support and labeled CXCR3 or fragment thereof may be detected in the presence and absence of a compound to be tested. CXCR3 may be labeled and detected using any techniques known in the art, for example, using the techniques described above for labeling and detecting gliadin.

These and other embodiments which will be apparent to those of skill in the art upon reading the specification provide the art with methods of screening for useful therapeutic agents and with methods of treating autoimmune and inflammation-associated diseases.

BRIEF DESCRIPTION OF THE DRAWINGS

FIG. 1A shows the amount of zonulin released after challenge. Gliadin challenge causes an increase in zonulin released. FIG. 1B shows the Trans Epithelial Electrical Resistance (TEER) after challenge. Gliadin challenge causes a decrease in TEER.

FIG. 4 shows the results of the protein bound to the gliadin affinity column is CXCR3, according to protein database search.

FIG. 6 shows the results of CXCR3 transfected HEK293 cells probed with anti-CXCR3 mAb (red trace) and IgG1 isotype control (blue trace).

FIG. 9 shows the effect of PT-gliadin on TEER and zonulin release in Black 6 wild type mice small intestine. FIG. 9A shows the TEER measurements made in snapwells and FIG. 9B shows the zonulin concentrations.

FIG. 10 shows the effect of PT-gliadin on TEER and zonulin release on small intestine from CXCR3 knockout mice.

DETAILED DESCRIPTION OF THE INVENTION

Figure 1A:
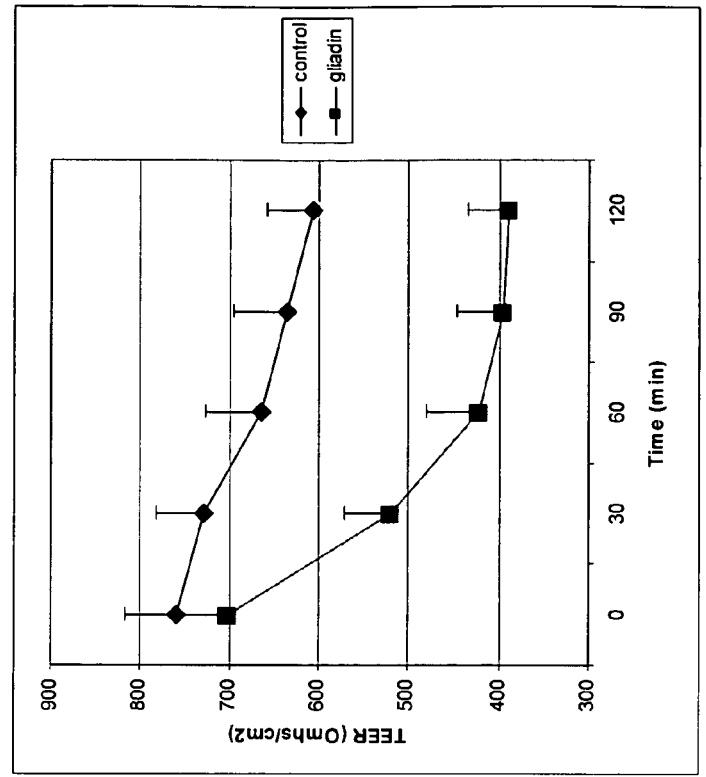
FIGS. 1A and 1B show results when jejunal intestinal fragments from wild-type mice mounted in microsnapwells were challenged with gliadin.

The inventors have discovered that the receptor known as CXCR3 is a physiological receptor for gliadin. This receptor not only binds to gliadin, but it also signals the release of zonulin and a decrease in trans-epithelial electrical resistance (TEER). These downstream effects indicate that the binding to gliadin is physiological.

Screening for modulators of CXRC3 signaling can be accomplished by a variety of techniques. Binding to CXRC3 to test compounds can be directly measured, or inhibition of binding of gliadin or another ligand to the receptor can be measured. Other ligands which can be used include IP10, MIG, and ITAC. Ligands can be labeled to facilitate measurement of binding. Assays may be in cell-free systems or in cell-based systems. Any binding assay format can be used, including formats where the receptor is attached to a solid support, either directly or indirectly.

Test compounds which can be tested are any compounds. The compounds may be tested as single compounds or in combinations of compounds. The compounds may be structurally identified or of unknown structure. The compounds may be novel or previously known. The compounds may be natural products or synthetic.

According to one embodiment of the invention the test compounds are fragments of gliadin. Gliadin is a family of proteins which are produced by wheat and other grains. Examples of gliadins are gliadin alpha, gamma, and omega. Gliadins are the aqueous alcohol-soluble storage proteins in the seed. There is great heterogeneity even within a single class of gliadins. At least six, seven, eight, nine, ten, eleven, fifteen, twenty, thirty, thirty-five, fifty, or seventy-five amino acid residues may be used in fragments of gliadin as test compounds. Fragments include any molecule which is less than full length. Fragments may be, e.g., synthesized or the result of proteolytic degradation. The following tables provide the sequences of a representative number of gliadins.

TABLE 1

Amino acid sequence of alpha-gliadin from
Triticum aestivum (NCBI accession no. CAB76964,
(SEQ ID NO:1))

```
  1 MVRVPVPQLQ PQNPSQQQPQ EQVPLVQQQQ FPGQQQPFPP
    QQPYPQPQPF PSQQPYLQLQ

61 PFPQPQLPYP QPQLPYPQPQ LPYPQPQPFR PQQPYPQSQP
    QYSQPQQPIS QQQQQQQQQQ

121 QQKQQQQQQQ QILQQILQQQ LIPCRDVVLQ QHSIAYGSSQ
    VLQQSTYQLV QQLCCQQLWQ

181 IPEQSRCQAI HNVVHAIILH QQQQQQQQQQ QQPLSQVSFQ
    QPQQQYPSGQ GSFQPSQQNP

241 QAQGSVQPQQ LPQFEEIRNL ALETLPAMCN VYIPPYCTIA
    PVGIFGTNYR
```

TABLE 2

Amino acid sequence of alpha-gliadin precursor
from Triticum turgidum subsp. durum (NCBI
accession no. CAI35909, (SEQ ID NO:2))

```
  1 MKTFLILALL AIVATTATTA VRVPVPQLQR QNPSQQQPQE
    QVPLVQQQF LGQQQPFPPQ

61 QPYPQPQPFP SQQPYLQLQP FPQPQLPYSQ PQPFRPQQPY
    PQPQPRYSQP QQPISQQQQQ

121 QHQQHQQHHQ EQQILQQILQ QQLIPCMDVV LQQHNIAHRR
    SQVLQQSTYQ LLQELCCQHL

181 WQIPEQSQCQ AIHNVVHAII PHQQQKQQQQ PSSQFSFQQP
    LQQYPLGQGS FRPSQQNPQA
```

TABLE 2-continued

Amino acid sequence of alpha-gliadin precursor
from Triticum turgidum subsp. durum (NCBI
accession no. CAI35909, (SEQ ID NO:2))

```
241 QGSVQPQQLP QFEEIRNLAL QTLPAMCNVY IPPYCTIAPF
    GIFGTN
```

TABLE 3

Amino acid sequence of alpha/beta-gliadin
precursor from Triticum aestivum (NCBI
accession no. AAA34280, (SEQ ID NO:3))

```
  1 MKTFLILVLL AIVATTATTA VRFPVPQLQP QNPSQQQPQE
    QVPLVQQQQF LGQQQPFPPQ

61 QPYPQPQPFP SQLPYLQLQP FPQPQLPYSQ PQPFRPQQPY
    PQPQPQYSQP QQPISQQQQQ

121 QQQQQQQQQQ QQQILQQILQ QQLIPCMDVV LQQHNIAHGR
    SQVLQQSTYQ LLQELCCQHL

181 WQIPEQSQCQ AIHNVVHAII LHQQQKQQQQ PSSQVSFQQP
    LQQYPLGQGS FRPSQQNPQA

241 QGSVQPQQLP QFEEIRNLAL QTLPAMCNVY IPPYCTIAPF
    GIFGTN
```

TABLE 4

Amino acid sequence of Gamma-gliadin
precursor from Triticum aestivum (NCBI accession
no. P21292, (SEQ ID NO:4))

```
  1 MKTLLILTIL AMATTIATAN MQVDPSGQVQ WPQQQPFPQP
    QQPFCQQPQR TIPQPHQTFH

61 HQPQQTFPQP QQTYPHQPQQ QFPQTQQPQQ PFPQPQQTFP
    QQPQLPFPQQ PQQPFPQPQQ

121 PQQPFPQSQQ PQQPFPQPQQ QFPQPQQPQQ SFPQQQQPAI
    QSFLQQQMNP CKNFLLQQCN

181 HVSLVSSLVS IILPRSDCQV MQQQCCQQLA QIPQQLQCAA
    IHSVAHSIIM QQEQQQGVPI

241 LRPLFQLAQG LGIIQPQQPA QLEGIRSLVL KTLPTMCNVY
    VPPDCSTINV PYANIDAGIG

301 GQ
```

TABLE 5

Amino acid sequence of Gamma-gliadin B precursor
from Triticum aestivum (NCBI accession no.
P06659, (SEQ ID NO:5))

```
  1 MKTLLILTIL AMAITIATAN MQADPSGQVQ WPQQQPFLQP
    HQPFSQQPQQ IFPQPQQTFP

61 HQPQQQFPQP QQPQQQFLQP RQPFPQQPQQ PYPQQPQQPF
    PQTQQPQQPF PQSKPQPQPF

121 PQPQQPQQSF PQQQPSLIQQ SLQQQLNPCK NFLLQQCKPV
    SLVSSLWSII LPPSDCQVMR

181 QQCCQQLAQI PQQLQCAAIH SVVHSIIMQQ EQQEQLQGVQ
    ILVPLSQQQQ VGQGILVQGQ

241 GIIQPQQPAQ LEVIRSLVLQ TLPTMCNVYV PPYCSTIRAP
    FASIVASIGG Q
```

TABLE 6

Amino acid sequence of Gamma-gliadin (Gliadin B-III) from *Triticum aestivum* (NCBI accession no. P04730, (SEQ ID NO:6))

```
  1 PQQPFPLQPQ QSFLWQSQQP FLQQPQQPSP QPQQVVQIIS
    PATPTTIPSA GKPTSAPFPQ

61 QQQQHQQLAQ QQIPVVQPSI LQQLNPCKVF LQQQCSPVAM
    PQRLARSQML QQSSCHVMQQ

121 QCCQQLPQIP QQSRYQAIRA IIYSIILQEQ QQVQGSIQSQ
    QQQPQQLGQC VSQPQQSQQQ

181 QLGQQPQQQQ LAQGTFLQPH QIAQLEVMTS IALRILPTMC
    SVNVPLYRTT TSVPFGVGTG

241 VGAY
```

TABLE 7

Amino acid sequence of Gamma-gliadin precursor from *Triticum aestivum* (NCBI accession no. P08453, (SEQ ID NO:7))

```
  1 MKTLLILTIL AMAITIGTAN IQVDPSGQVQ WLQQQLVPQL
    QQPLSQQPQQ TFPQPQQTFP

61 HQPQQQVPQP QQPQQPFLQP QQPFPQQPQQ PFPQTQQPQQ
    PFPQPQQPF PQTQQPQQPF

121 PQQPQQPFPQ TQQPQQPFPQ LQQPQQPFPQ PQQQLPQPQQ
    PQQSFPQQQR PFIQPSLQQQ

181 LNPCKNILLQ QSKPASLVSS LWSIIWPQSD CQVMRQQCCQ
    QLAQIPQQLQ CAAIHSVVHS

241 IIMQQQQQQQ QQQGIDIFLP LSQHEQVGQG SLVQGQGIIQ
    PQQPAQLEAI RSLVLQTLPS

301 MCNVYVPPEC SIMRAPFASI VAGIGGQ
```

TABLE 8

Amino acid sequence of Gamma-gliadin B-I precursor from *Triticum aestivum* (NCBI accession no. P04729, (SEQ ID NO:8))

```
  1 MKTFLVFALI AVVATSAIAQ METSCISGLE RPWQQQPLPP
    QQSFSQQPPF SQQQQQPLPQ

61 QPSFSQQQPP FSQQQPILSQ QPPFSQQQQP VLPQQSPFSQ
    QQQLVLPPQQ QQQQLVQQQI

121 PIVQPSVLQQ LNPCKVELQQ QCSPVAMPQR LARSQMWQQS
    SCHVMQQCC QQLQQIPEQS

181 RYEAIRAIIY SIILQEQQQG FVQPQQQQPQ QSGQGVSQSQ
    QQSQQQLGQC SFQQPQQQLG

241 QQPQQQQQQQ VLQGTFLQPH QIAHLEAVTS IALRTLPTMC
    SVNVPLYSAT TSVPFGVGTG

301 VGAY
```

TABLE 9

Amino acid sequence of Gamma-gliadin precursor from *Triticum aestivum* (NCBI accession no. P08079, (SEQ ID NO:9))

```
  1 MKTLLILTIL AMAITIGTAN MQVDPSSQVQ WPQQQPVPQP
    HQPFSQQPQQ TFPQPQQTFP
```

TABLE 9-continued

Amino acid sequence of Gamma-gliadin precursor from *Triticum aestivum* (NCBI accession no. P08079, (SEQ ID NO:9))

```
 61 HQPQQQFPQP QQPQQQFLQP QQPFPQQPQQ PYPQQPQQPF
    PQTQQPQQLF PQSQQPQQQF

121 SQPQQQFPQP QQPQQSFPQQ QPPFIQPSLQ QQVNPCKNFL
    LQQCKPVSLV SSLWSMIWPQ

181 SDCQVMRQQC CQQLAQIPQQ LQCAAIHTII HSIIMQQEQQ
    EQQQGMHILL PLYQQQQVGQ

241 GTLVQGQGII Q
```

TABLE 10

Amino acid sequence of Alpha/beta-gliadin MM1 precursor (Prolamin) from *Triticum aestivum* (NCBI accession no. P18573, (SEQ ID NO:10))

```
  1 MKTFLILALL AIVATTARIA VRVPVPQLQP QNPSQQQPQE
    QVPLVQQQQF PGQQQPFPPQ

61 QPYPQPQPFP SQQPYLQLQP FPQPQLPYPQ PQLPYPQPQL
    PYPQPQPFRP QQPYPQSQPQ

121 YSQPQQPISQ QQQQQQQQQQ QKQQQQQQQQ ILQQILQQQL
    IPCRDVVLQQ HSIAYGSSQV

181 LQQSTYQLVQ QLCCQQLWQI PEQSRCQAIH NVVHAIILHQ
    QQQQQQQQQQ QPLSQVSFQQ

241 PQQQYPSGQG SFQPSQQNPQ AQGSVQPQQL PQFEEIRNLA
    LETLPAMCNV YIPPYCTIAP

301 VGIFGTN
```

TABLE 11

Amino acid sequence of Alpha/beta-gliadin clone PTO-A10 (Prolamin) from *Triticum aestivum* (NCBI accession no. P04728, (SEQ ID NO:11))

```
  1 PQPQPQYSQP QQPISQQQQQ QQQQQQQQQQ EQQILQQILQ
    QQLIPCMDVV LQQHNIAHGR

61 SQVLQQSTYQ LLQELCCQHL WQIPEQSQCQ AIHNVVHAII
    LHQQQQKQQQ QPSSQFSFQQ

121 PLQQYPLGQG SFRPSQQNPQ AQGSVQPQQL PQFEIRNLAL
    QTLPAMCNVY IPPYCTIAPF

181 GIFGTN
```

TABLE 12

Amino acid sequence of Alpha/beta-gliadin clone PW8142 precursor (Prolamin) from *Triticum aestivum* (NCBI accession no. P04727, (SEQ ID NO:12))

```
  1 MKTFLILALV ATTATTAVRV PVPQLQPKNP SQQQPQEQVP
    LVQQQQFPGQ QQQFPPQQPY

61 PQPQPFPSQQ PYLQLQPFPQ PQPFLPQLPY PQPQSFPPQQ
    PYPQQRPKYL QPQQPISQQQ

121 AQQQQQQQQQ QQQQQQQQIL QQILQQQLIP CRDVVLQQHN
    IAHASSQVLQ QSTYQLLQQL

181 CCQQLLQIPE QSRCQAIHNV VHAIIMHQQE QQQQLQQQQQ
    QQLQQQQQQQ QQQQQPSSQV
```

TABLE 12-continued

Amino acid sequence of Alpha/beta-gliadin clone PW8142 precursor (Prolamin) from *Triticum aestivum* (NCBI accession no. P04727, (SEQ ID NO:12))

```
241 SFQQPQQQYP SSQGSFQPSQ QNPQAQGSVQ PQQLPQFAEI
    RNLALQTLPA MCNVYIPPHC

301 STTIAPFGIF GTN
```

TABLE 13

Amino acid sequence of Alpha/beta-gliadin clone PW1215 precursor (Prolamin) from *Triticum aestivum* (NCBI accession no. P04726, (SEQ ID NO:13))

```
  1 MKTFLILALL AIVATTATTA VRVPVPQPQP QNPSQPQPQG
    QVPLVQQQQF PGQQQQFPPQ

61 QPYPQPQPFP SQQPYLQLQP FPQPQPFPPQ LPYPQPPPFS
    PQQPYPQPQP QYPQPQQPIS

121 QQQAQQQQQ QQQQQQQQQQ QQILQQILQQ QLIPCRDVVL
    QQHNIAHARS QVLQQSTYQP

181 LQQLCCQQLW QIPEQSRCQA IHNVVHAIIL HQQQRQQQPS
    SQVSLQQPQQ QYPSGQGFFQ

241 PSQQNPQAQG SVQPQQLPQF EEIRNLALQT LPRMCNVYIP
    PYCSTTIAPF GIFGTN
```

TABLE 14

Amino acid sequence of Alpha/beta-gliadin A-IV precursor (Prolamin) from *Triticum aestivum* (NCBI accession no. P04724, (SEQ ID NO:14))

```
  1 MKTFLILALR AIVATTATIA VRVPVPQLQP QNSQQQPQK
    QVPLVQQQQF PGQQQPFPPQ

61 QPYPQQQPFP SQQPYMQLQP FPQPQLPYPQ PQLPYPQPQP
    FRPQQSYPQP QPQYSQPQQP

121 ISQQQQQQQQ QQQQQQQILQ QILQQQLIPC RDVVLQQHSI
    AHGSSQVLQQ STYQLVQQFC

181 CQQLWQIPEQ SRCQAIHNVV HAIILHQQQQ QQQQQQQQQ
    QPLSQVCFQQ SQQQYPSGQG

241 SFQPSQQNPQ AQGSVQPQQL PQFEEIRNLA LETLPAMCNV
    YIPPYCTIAP VGIFGTN
```

TABLE 15

Amino acid sequence of Alpha/beta-gliadin A-III precursor (Prolamin) from *Triticum aestivum* (NCBI accession no. P04723, (SEQ ID NO:15))

```
  1 MKTFLILALL AIVATTATSA VRVPVPQLQP QNPSQQQPQE
    QVPLMQQQQ FPGQQEQFPP

61 QQPYPHQQPF PSQQPYPQPQ PFPPQLPYPQ TQPFPPQQPY
    PQPQPQYPQP QQPISQQQAQ

121 QQQQQQQTLQ QILQQQLIPC RDVVLQQHNI AHASSQVLQQ
    SSYQQLQQLC CQQLFQIPEQ

181 SRCQAIHNVV HAIILHHHQQ QQQQPSSQVS YQQPQEQYPS
    GQVSFQSSQQ NPQAQGSVQP

241 QQLPQFQEIR NLALQTLPAM CNVYIPPYCS TTIAPFGIFG
    TN
```

TABLE 16

Amino acid sequence of Alpha/beta-gliadin A-II precursor (Prolamin) from *Triticum aestivum* (NCBI accession no. P04722, (SEQ ID NO:16))

```
  1 MKTFPILALL AIVATTATTA VRVPVPQLQL QNPSQQQPQE
    QVPLVQEQQF QGQQQPFPPQ

61 QPYPQPQPFP SQQPYLQLQP FPQPQLPYPQ PQPFRPQQPY
    PQPQPQYSQP QQPISQQQQQ

121 QQQQQQQQQQ ILQQILQQQL IPCRDVVLQQ HNIAHGSSQV
    LQESTYQLVQ QLCCQQLWQI

181 PEQSRCQAIH NVVHAIILHQ QHHHHQQQQQ QQQQQPLSQV
    SFQQPQQQYP SGQGFFQPSQ

241 QNPQAQGSFQ PQQLPQFEEI RNLALQTLPA MCNVYIPPYC
    TIAPFGIFGT N
```

TABLE 17

Amino acid sequence of Alpha/beta-gliadin A-I precursor (Prolamin) from *Triticum aestivum* (NCBI accession no. P04721, (SEQ ID NO:17))

```
  1 MKTFLILALL AIVATTATTA VRVPVPQLQP QNPSQQQPQE
    QVPLVQQQQF LGQQQPFPPQ

61 QPYPQPQPFP SQQPYLQLQP FLQPQLPYSQ PQPFRPQQPY
    PQPQPQYSQP QQPISQQQQQ

121 QQQQQQQQQQ QQQQIIQQIL QQQLIPCMDV VLQQHNIVHG
    KSQVLQQSTY QLLQELCCQH

181 LWQIPEQSQC QAIHNVVHAI ILHQQQKQQQ QPSSQVSFQQ
    PLQQYPLGQG SFRPSQQNPQ

241 AQGSVQPQQL PQFEEIRNLA RK
```

TABLE 18

Amino acid sequence of gamma gliadin from *Triticum aestivum* (NCBI accession no. AAQ63860, (SEQ ID NO:18))

```
  1 MNIQVDPSSQ VPWPQQQPFP QPHQPFSQQP QQTFPQPQQT
    FPHQPQQQFS QPQQPQQQFI

61 QPQQPFPQQP QQTYPQRPQQ PFPQTQQPQQ PFPQSQQPQQ
    PFPQPQQQFP QPQQPQQSFP

121 QQQPSLIQQS LQQQLNPCKN FLLQQCKPVS LVSSLWSMIL
    PRSDCQVMRQ QCCQQLAQIP

181 QQLQCAAIHS IVHSIIMQQE QQEQRQGVQI LVPLSQQQQV
    GQGTLVQGQG IIQPQQPAQL

241 EVIRSLVLQT LATMCNVYVP PYCSTIRAPF ASIVAGIGGQ
    YR
```

TABLE 19

Amino acid sequence of Omega-gliadin from *Triticum monococcum* (NCBI accession no. P02865, (SEQ ID NO:19))

```
  1     ARQLNPSDQE LQSPQQLYPQ QPYPQQPY
```

Fragments of gliadin that may be used in the practice of the invention include, but are not limited to, Leu-Gln-Leu-Gln-Pro-Phe-Pro-Gln-Pro-Gln-Leu-Pro-Tyr-Pro-Gln-Pro-Gln-Leu-Pro-Tyr-Pro-Gln-Pro-Gln-Leu-Pro-Tyr-Pro-Gln-Pro-Gln-Pro-Phe, which corresponds to amino acids 57-89 of the alpha-gliadin sequence of Table 1, and Leu-Gly-Gln-Gln- Gln-Pro-Phe-Pro-Pro-Gln-Gln-Pro-Tyr (SEQ ID NO:20), which corresponds to amino acids 32-44 of the alpha-gliadin sequence of Table 1 with the proline at position 32 of the wildtype alpha-gliadin sequence mutated to a leucine. Other suitable fragments of gliadin may be prepared, for example, by digesting a purified gliadin with proteolytic enzymes (e.g., pepsin, trypsin or mixtures thereof) and isolating peptides. Peptides may be isolated using any technique known in the art such as reverse phase high pressure liquid chromatography (RP-HPLC).

Modulators of CXCR3 signaling may be inhibitors, enhancers, or agonists. Inhibitors are useful for treating diseases characterized by inflammation, including autoimmune diseases and particularly including celiac disease. Enhancers or agonists can be used for increasing permeability of a tissue to a desired agent, e.g., a therapeutic agent which is less than optimally absorbed.

Antibodies to CXRC3 can be therapeutically by administration to patients in need thereof. Such patients include those with gluten-related diseases as well as diseases associated with inflammation and autoimmunity. Administration can be by any means known in the art for administration of antibodies. Such methods include, but are not limited to intravenous, intramuscular, and subcutaneous administration. Any form of antibodies known in the art can be used. The antibodies can be polyclonal or monoclonal. They can be, e.g., humanized or human or chimeric or recombinant. The antibodies can be of any isotype. They may be single chain antibodies, or fragments of antibodies such as $F(ab')_2$.

Signaling by CXCR3 can be measured by any means known in the art. Signaling events which can be determined include decrease in TEER, increase in zonulin release, microglia recruitment, tyrosine kinase phosphorylation and chemotaxis, and increase in MMP-2 and MMP-9 gelatinolytic activity in cell-conditioned media.

The invention provides methods of identifying agents, compounds or lead compounds for agents active at the level of CXCR3-ligand interaction. Generally, screening methods of the invention involve assaying for compounds which modulate the interaction of CXCR3 and ligand (e.g., gliadin or fragment thereof). A wide variety of assays for binding agents is provided including labeled in vitro protein-ligand binding assays, cell based assays, immunoassays, etc. A wide variety of formats may be used, including co-immunoprecipitation, 2-hybrid transactivation, fluorescent polarization, NMR, fluorescent resonance energy transfer (FRET), transcriptional activation, etc. For example, a wide variety of NMR-based methods are available to rapidly screen libraries of small compounds for binding to protein targets (Hajduk, P. J., et al. Quarterly Reviews of Biophysics, 1999, 32 (3): 211-40). In some embodiments, methods of the invention may be automated (e.g., high throughput screening) and may be used to screen chemical libraries for lead compounds. Identified compounds may be used to treat diseases involving CXCR3 signaling, for example, autoimmune diseases. Compounds identified by the methods of the invention may be further optimized to modulate CXCR3 signaling, for example, may be derivatized. Multiple iterations of screening and derivatization may be employed to optimize the modulation of CXCR3 signaling.

In vitro ligand binding assays employ a mixture of components including CXCR3 or fragment thereof and ligand (e.g., gliadin or fragment thereof). CXCR3 and/or gliadin may be provided as fusion proteins (e.g., with purification tags such as 6-His). Assay mixtures typically further comprise a compound to be tested for CXCR3 modulating activity. Compounds to be tested may be of any kind known to those skilled in the art, for example, may be organic compounds, peptides, proteins, nucleic acids, lipids, carbohydrates and mixtures thereof. A variety of other reagents may also be included in the mixture including, but not limited to, salts, buffers, neutral proteins, e.g. albumin, detergents, protease inhibitors, nuclease inhibitors, antimicrobial agents, etc.

In general, assay mixtures may be incubated under conditions in which, but for the presence of the compound to be tested, CXCR3 specifically binds the ligand (e.g., gliadin or fragment thereof) with a reference binding affinity. The mixture components can be added in any order that provides for the requisite bindings and incubations may be performed at any temperature which facilitates optimal binding. Incubation periods are likewise selected for optimal binding. In some embodiments, incubation periods may be minimized to facilitate rapid, high-throughput screening.

After incubation, the effect of the compound to be tested on the CXCR3-ligand binding may be detected by any convenient way. For example, CXCR3 or ligand may be immobilized, and the other labeled; then in a solid-phase format, any of a variety of methods may be used to detect the label depending on the nature of the label and other assay components, e.g. through optical or electron density, radiative emissions, nonradiative energy transfers, etc. or indirectly detected with antibody conjugates, etc.

A difference in the binding affinity of CXCR3 and the ligand in the absence of the compound to be tested as compared with the binding affinity in the presence of the compound to be tested indicates that the compound modulates the binding of CXCR3 to the ligand. A difference, as used herein, is statistically significant and preferably represents at least a 50%, 60%, 70%, 80%, or 90% difference.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLE 1

In order to identify the putative receptor activated by gliadin, we performed experiments using a gliadin affinity column through which intestinal cell lysates were loaded. We eluted proteins with a step salt gradient. Three clear protein bands were observed on SDS-polyacrylamide gels with molecular weights of 97, 90, and 83 kDa. The observed proteins eluted at 0.2 M and 0.3 M NaCl off the affinity column. Mass spectrometry analysis of proteins that bound to the column identified XP_125429 in the NCBI sequence database (see Table 20). This sequence includes a precursor of the CXCR3 receptor and implicates the CXCR3 receptor as one of the proteins engaged by gladin (see FIG. 4).

TABLE 20

Amino acid sequence of the protein identified by fragment sequencing (NCBI accession non. XP_125249 (SEQ ID NO:21))

```
  1  MASGADSKGD DLSTAILKQK NRPNRLIVDE AINEDNSVVS
     LSQPKMDELQ LFRGDTVLLK

61  GKKRREAVCI VLSDDTCSDE KIRMNRVVRN NLRVRLGDVI
     SIQPCPDVKY GKRIHVLPID

121  DTVEGITGNL FEVYLKPYFL EAYRPIRKGD IFLVRGGMRA
     VEFKVVETDP SPYCIVAPDT

181  VIHCEGEPIK REDEEESLNE VGYDDIGGCR KQLAQIKEMV
     ELPLRHPALF KAIGVKPPRG

241  ILLYGPPGTG KTLIARAVAN ETGAFFFLIN GPEIMSKLAG
     ESESNLRKAF EEAEKNAPAI
```

TABLE 20-continued

Amino acid sequence of the protein identified by fragment sequencing (NCBI accession non. XP_125249 (SEQ ID NO:21))

```
301 IFIDELDAIA PKREKTHGEV ERRIVSQLLT LMDGLKQRAH
    VIVMAATNRP NSIDPALRRF

361 GRFDREVDIG IPDATGRLEI LQIHTKNMKL ADDVDLEQVA
    NETHGHVGAD LAALCSEAAL

421 QAIRKKMDLI DLEDETIDAE VMNSLAVTMD DFRWALSQSN
    PSALRETVVE VPQVTWEDIG

481 GLEDVKRELQ ELVQYPVEHP DKFLKFGMTP SKGVLFYGPP
    GCGKTLLAKA IANECQANFI

541 SIKGPELLTM WFGESEANVR EIFDKARVLF FDELDSIAKA
    RGGNIGDGGG AADRVINQIL

601 TEMDGMSTKK NVFIIGATNR PDIIDPAILR PGRLDQLIYI
    PLPDEKSRVA ILKANLRKSP

661 VAKDVDLEFL AKMTNGFSGA DLTEICQRAC KLAIRESIES
    EIRRERERQT NPSAMEVEED

721 DPVPEIRRDH FEEAMRFARR SVSDNDIRKY EMFAQTLQQS
    RGFGSFRFPS GNQGGAGPSQ

781 GSGGGTGGSV YTEDNDDDLY G
```

Human CXCR3 has 368 amino acid residues and a calculated molecular weight of 40,459. The sequences of human CXCR3 and mouse CXCR3 are provided in the following tables.

TABLE 21

Amino acid sequence of CXCR3 from *Homo sapiens* (NCBI accession no. AAH34403, (SEQ ID NO:22))

```
  1 MVLEVSDHQV LNDAEVAALL ENFSSSYDYG ENESDSCCTS
    PPCPQDFSLN FDRAFLPALY

61 SLLFLLGLLG NGAVAAVLLS RRTALSSTDT FLLHLAVADT
    LLVLTLPLWA VDAAVQWVFG

121 SGLCKVAGAL FNINFYAGAL LLACISFDRY LNIVHATQLY
    RRGPPARVTL TCLAVWGLCL

181 LFALPDFIFL SAHHDERLNA THCQYNFPQV GRTALRVLQL
    VAGFLLPLLV MAYCYAHILA

241 VLLVSRGQRR LRAMRLVVVV VVAFALCWTP YHLVVLVDIL
    MDLGALARNC GRESRVDVAK

301 SVTSGLGYMH CCLNPLLYAF VGVKFRERMW MLLLRLGCPN
    QRGLQRQPSS SRRDSSWSET

361 SEASYSGL
```

TABLE 21

Amino acid sequence of CXCR3 from *Mus musculus* (NCBI accession no. NP_034040, (SEQ ID NO:23))

```
  1 MYLEVSERQV LDASDFAFLL ENSTSPYDYG ENESDFSDSP
    PCPQDFSLNF DRTFLPALYS

61 LLFLLGLLGN GAVAAVLLSQ RTALSSTDTF LLHLAVADVL
    LVLTLPLWAV DAAVQWVFGP

121 GLCKVAGALF NINFYAGAFL LACISFDRYL SIVHATQIYR
    RDPRVRVALT CIVVWGLCLL
```

TABLE 21-continued

Amino acid sequence of CXCR3 from *Mus musculus* (NCBI accession no. NP_034040, (SEQ ID NO:23))

```
181 FALPDEIYLS ANYDQRLNAT HCQYNFPQVG RTALRVLQLV
    AGFLLPLLVM AYCYAHILAV

241 LLVSRGQRRF RAMRLVVVVV AAFAVCWTPY HLVVLVDILM
    DVGVLARNCG RESHVDVAKS

301 VTSGMGYMHC CLNPLLYAFV GVKFREQMWM LFTRLGRSDQ
    RGPQRQPSSS RRESSWSETT

361 EASYLGL
```

CXCR3 is a G-protein coupled receptor which is known to function as a receptor of SCYB9, SCYB10, and SCYB11, also known as MIG, IP10, and ITAC, cytokines implicated in inflammation. The receptor is also identified as CD183, GPR9, CKR-L2. The amino acid sequence of the receptor is shown as SEQ ID NO: 23. Human variants are known such as a R292Q and an A363T polymorphisms see SEQ ID NO:22.

Methods

We linked α-gliadin (a gift from Dr. Donald D. Kasarda) to CARBOXYLINK™. (Pierce Biotechnology, Rockford, Ill.) coupling gel to form an affinity column.

We prepared human intestine mucous membranes using protease inhibitors and a standard protocol.

One protocol which can be used involves the following steps: Tissues are washed with buffer D (20 mmol·L$^{-1}$ Tris-HCl, 20 mmol·L$^{-1}$ EDTA, 250 mmol·L$^{-1}$ sucrose, pH 7.5) homogenized in buffer E (buffer D containing 5 mg·L$^{-1}$ leupeptin, 2 mg·L$^{-1}$ aprotinin, 1 mg·L$^{-1}$ pepstatin, 10 mg·L$^{-1}$ phenylmethylsulfonylfluoride (PMSF), and centrifuged at 5000×g, 4° C. for 10 min. Supernatants are centrifuged at 12000×g, 4° C. for 45 min. Precipitates are discarded and supernatants are centrifuged at 30000×g, 4° C. for an additional 90 min. Precipitates are dissolved in buffer E with 5 g·L$^{-1}$ 3[(3-cholamidopropyl) dimethylammonio]-1-propanesulfonate (CHAPS), sitting on ice for 60 min. with gentle mixing every five minutes.

EXAMPLE 2

Figure 1B:
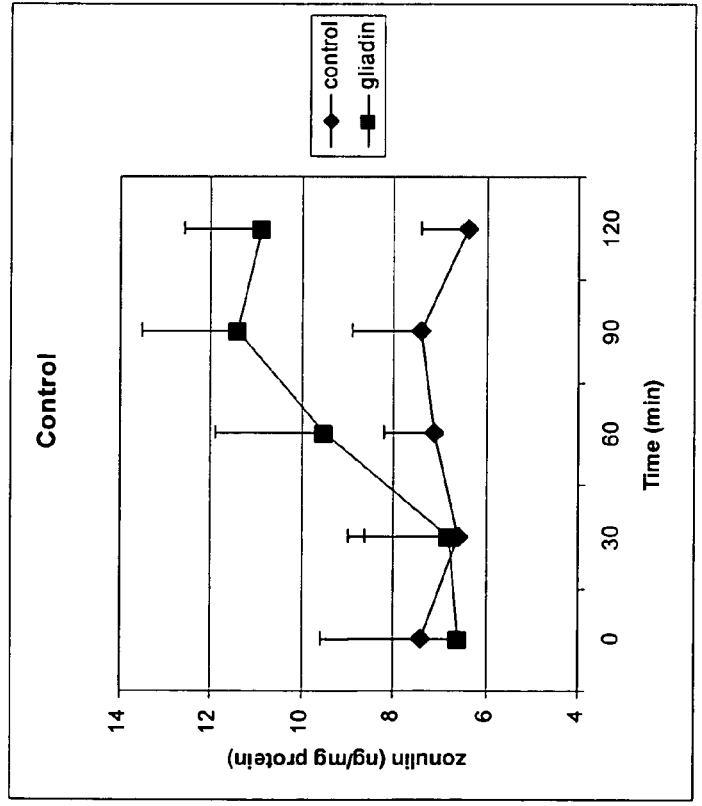

Intestinal fragments isolated from normal mice, mounted on microsnapwells, and exposed to gliadin react by releasing zonulin. FIG. 1A. Following zonulin release, the intestinal permeability increases, suggesting a loss of the mucosal barrier function. FIG. 1B. This so-called "gluten effect" is detectable only when the protein is added to the surface (luminal side) of the intestine, suggesting that gliadin interacts with a receptor present on the enterocyte brush border.

Figure 2:
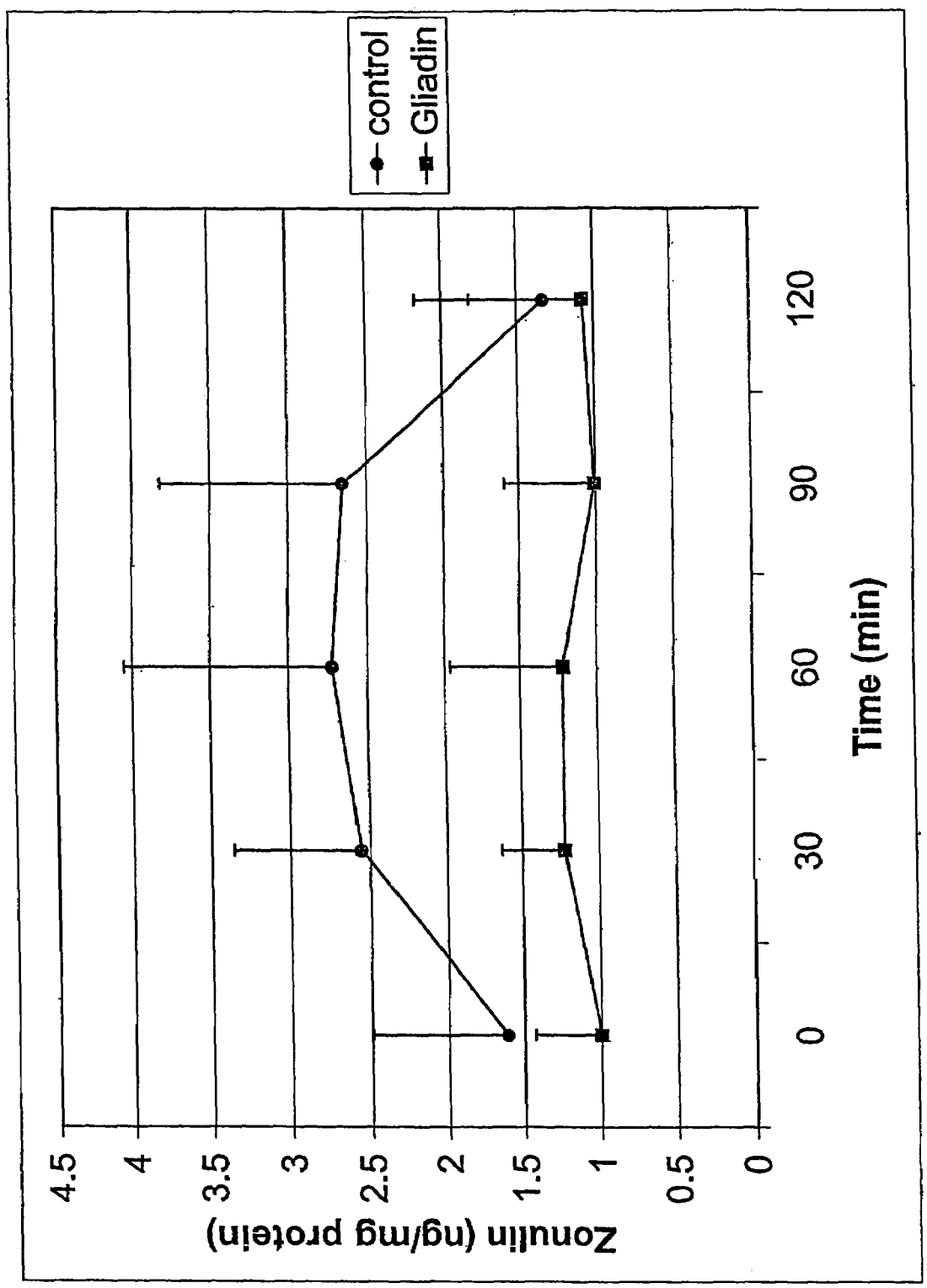
FIG. 2 shows the zonulin released after gliadin challenge of endoscopic jejunal biopsies from CXCR3-deficient mice. Gliadin challenge failed to lead to zonulin release. Compare to FIG. 1A.
Figure 3:
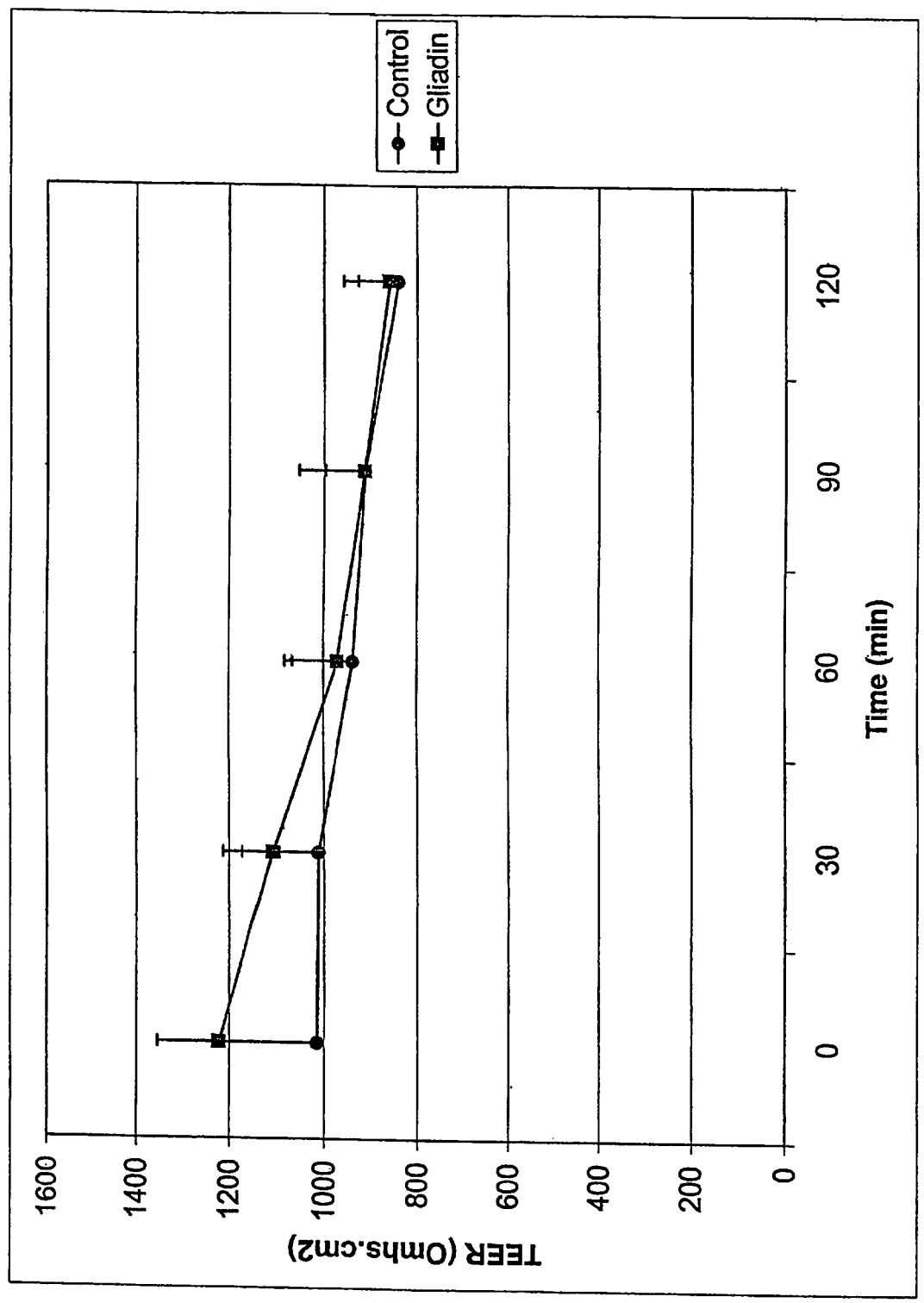
FIG. 3 shows the TEER after gliadin challenge of endoscopic jejunal biopsies from CXCR3-deficient mice. Gliadin challenge failed to decrease TEER. Compare to FIG. 1B.
Figures 5A, 5B:
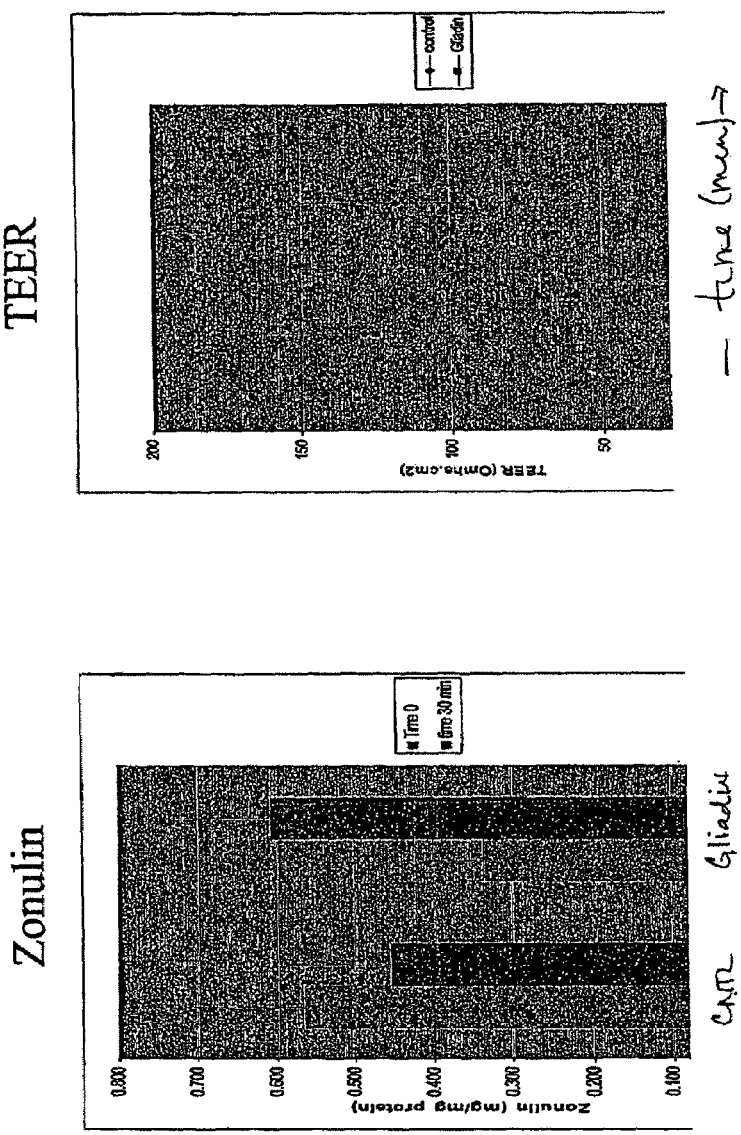
FIG. 5A and FIG. 5B, respectively, show the zonulin levels and TEER of B6 wild type mice challenged with gliadin.
Figures 5C, 5D:
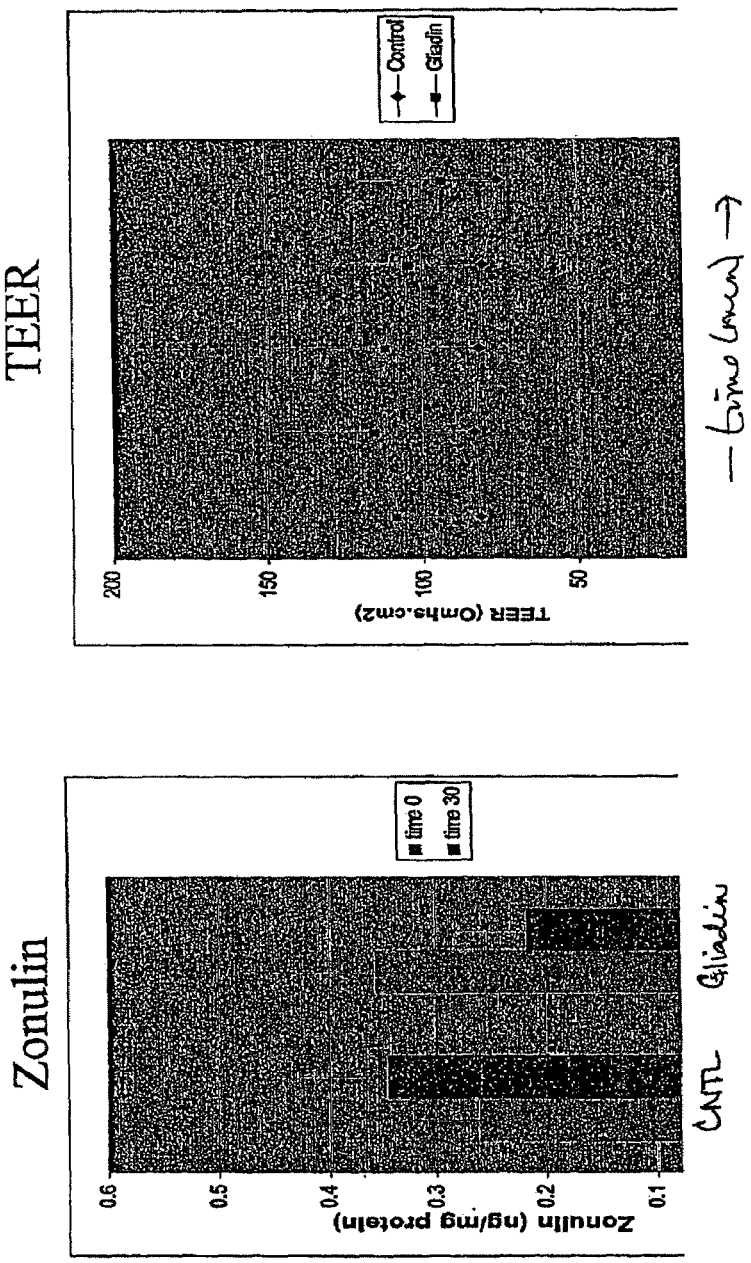
FIG. 5C and FIG. 5D, repectively, show the zonulin levels and TEER of CXCR3 knock-out mice (n=20) challenged with gliadin. The CXCR3 knock-out mice do not respond to gliadin and do not release zonulin, and accordingly, do not exhibit an increase in intestinal permeability. In contrast, the wild-type cohort responds to gliadin, releases zonulin and, therefore, does exhibit an increase in intestinal permeability.

To confirm the hypothesis that CXCR3 is the gliadin target receptor that needs to be activated in order to release zonulin, experiments were conducted using a CXCR3 knock out mouse model. Intestinal tissues isolated from these animals, mounted in the microsnapwell system, and exposed to gliadin failed to release zonulin and, consequently, no changes in intestinal permeability were detected. FIGS. 2 and 3. These results confirm the hypothesis that CXCR3 is a gliadin target receptor involved in zonulin release.

The "microsnapwell system," a polarized model, is used to study the intestinal barrier function using human intestinal biopsies. The system evaluates the intestinal permeability of endoscopic jejunal biopsies by measuring the Trans Epithelial Electrical Resistance (TEER).

EXAMPLE 3

In vitro experiments using HEK cells transfected with CXCR3 were performed to study gliadin binding to the receptor by immunofluorescence (IF) microscopy. The in vitro IF experiments showed that gliadin bound on cells transfected with CXCR3 but not on cells transfected with vector alone.

Figure 6A:
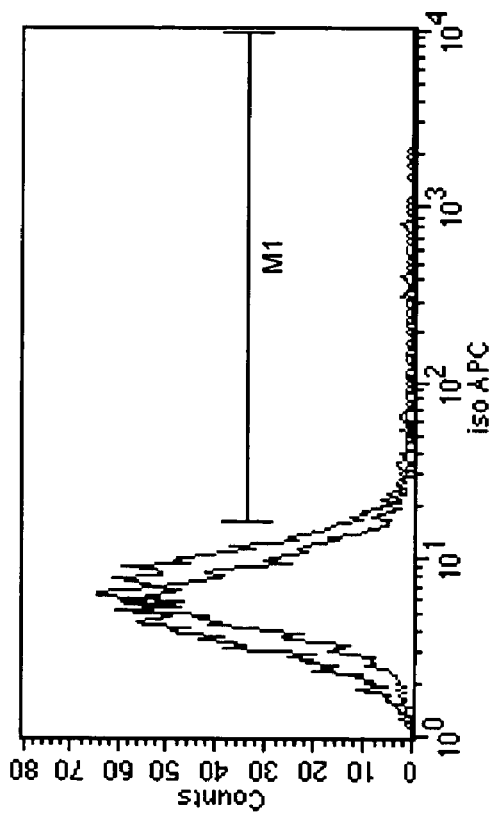
FIG. 6A shows cells transfected with vector.
Figure 6B:
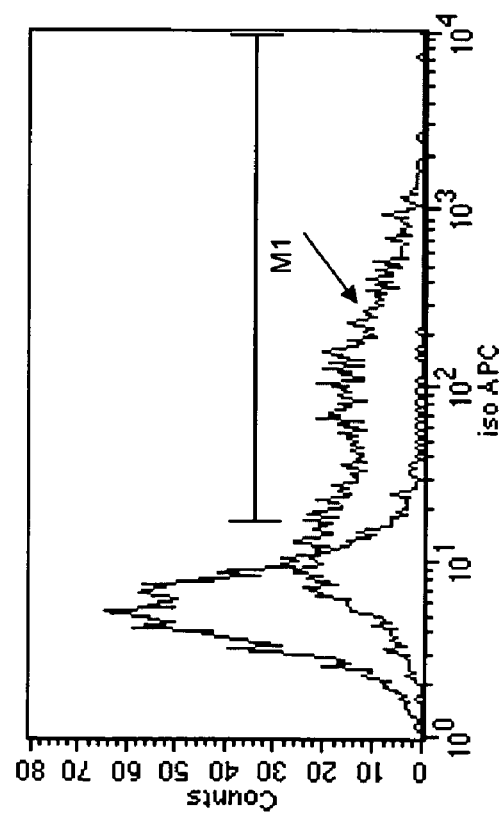
FIG. 6B shows cells transfected with vector expressing CXCR3.

As shown in FIG. 6, HEK293 cells transfected with vector expressing CXCR3 were specifically labeled with anti-CXCR3 mAb. The human CXCR3 sequence was inserted into pc DNA 3.1 (Invitrogen Corporation, Carlsbad, Calif.) under the control of a CMV1 promoter. Red trace shows results obtained with anti-CXCR3 mAb (marked with an arrow in 6B), blue trace shows results obtained with IgG1 isotype control. FIG. 6A shows the control transfection with vector alone while FIG. 6B shows the results obtained with vector expressing CXCR3. With vector alone, CXCR3 expression was 4.42%, mean 11.9 (FIG. 6A). In contrast, with cells transfected with vector expressing CXCR3, CXCR3 expression was 61.78%, mean 95.5.

Figures 7, 7A, 7B, 7C:
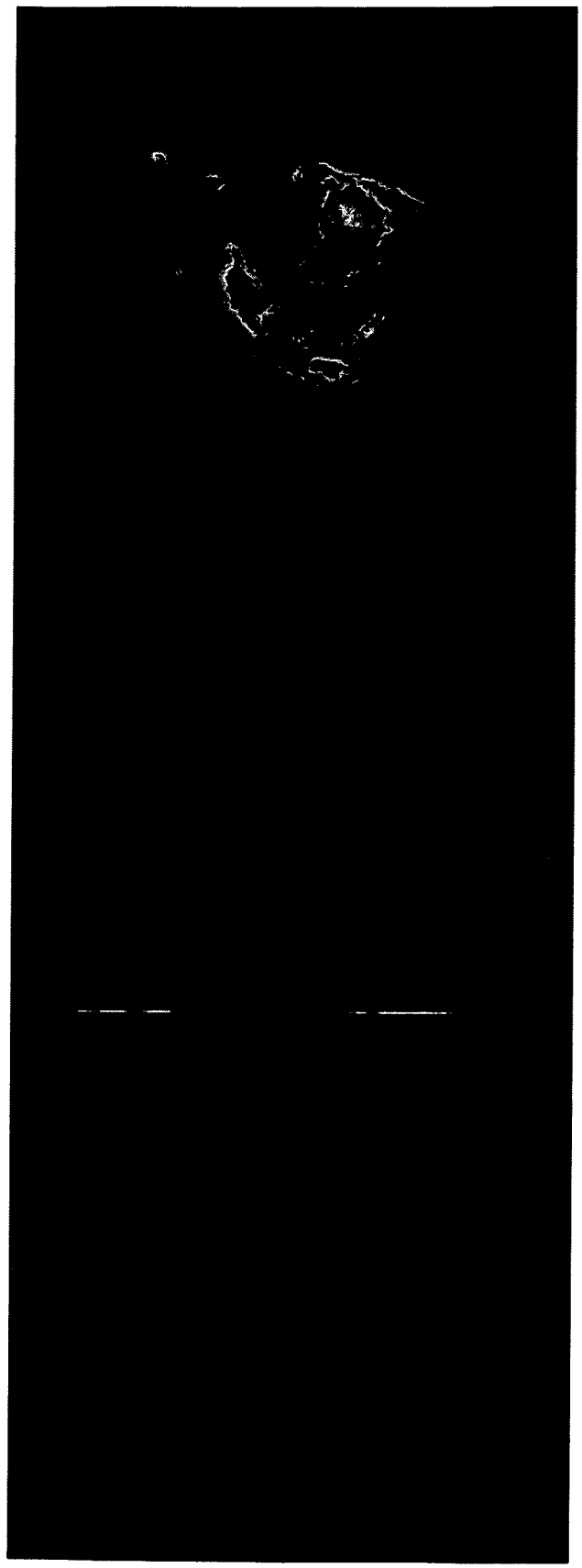
FIG. 7 shows the results of fluorescence microscopy of cells transfected probed with DAPI (blue), RITC-labeled anti-CXCR3 monoclonal antibody (red), and FITC-labeled PT-gliadin (green). Panel A shows cells transfected with control vector and probed with DAPI and anti-CXCR3 monoclonal antibody, Panel B shows cells transfected with CXCR3-expressing vector and probed with anti-CXCR3 monoclonal antibody, and Panel C shows cells transfected with CXCR3-expressing vector and probed with anti-CXCR3 monoclonal antibody and FITC-labeled PT-gliadin.

When cells transfected with vector expressing CXCR3 were contacted with fluorescently labeled gliadin, the gliadin bound to the cells and not to the control cells that did not express CXCR3, thus PT-Gliadin co-localizes with CXCR3 in HEK293 transfected cells. In FIG. 7, nuclei were stained with DAPI (blue), CXCR3 were stained with monoclonal antibody labeled with RITC (red), and PT-Gliadin was labeled with FITC (green). Panel A shows nuclear staining only with cells transfected with control vector. Panel B shows the staining on the outside of the cells transfected with vector expressing CXCR3 and contacted with RITC-labeled monoclonal antibody specific for CXCR3. When the cells in Panel B were contacted with FITC-labeled gliadin, the gliadin co-localized with CXCR3.

EXAMPLE 4

Figure 8:
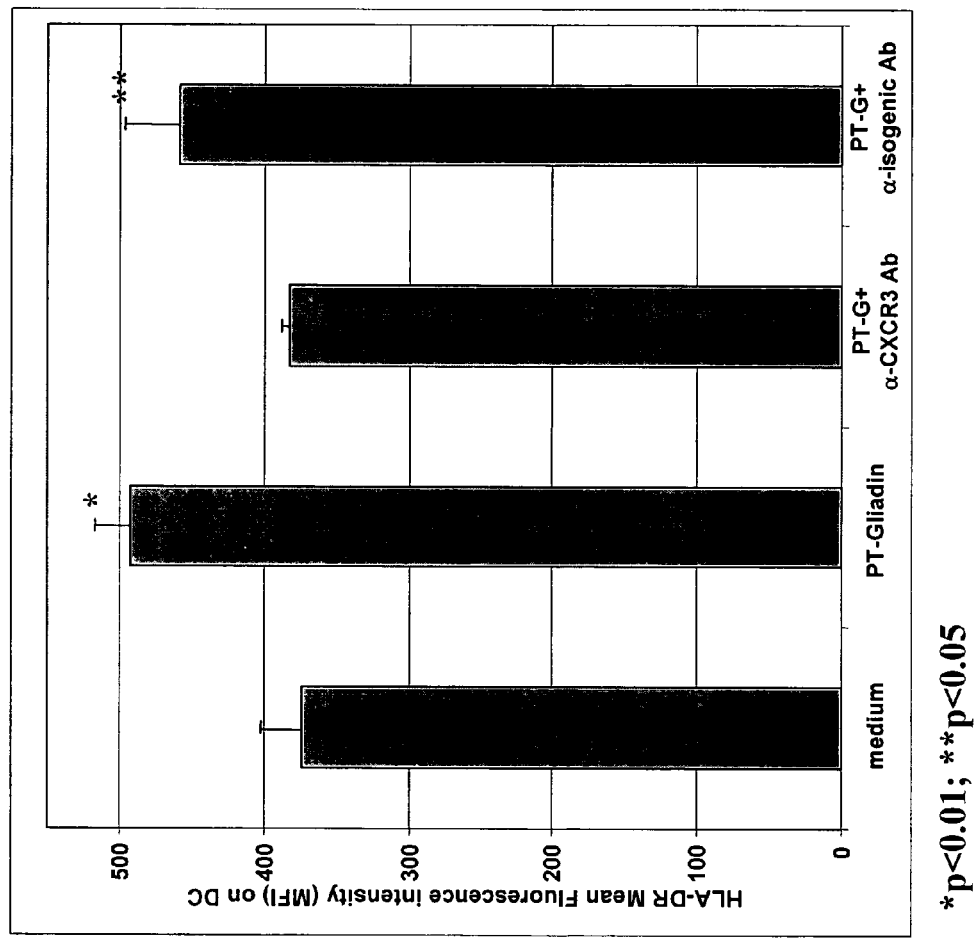
FIG. 8 shows the results of the effect of gliadin digested with pepsin and trypsin (PT-Gliadin) on HLA-DR expression in dendritic cells from normal volunteers.

Finally, the expression of co-stimulatory markers on peripheral blood mononuclear cells (PBMC) was studied in both normal subjects and patients affected by autoimmunity (celiac disease and type 1 diabetes). PBMC from autoimmune patients exposed to gliadin showed increase expression of co-stimulatory markers CD40, CD80, and CD86, and DR. The stimulation of DR expression (but not of the other markers) was prevented by blocking the CXCR3 receptor using specific antibodies. FIG. 8 shows the effect of PT-gliadin on HLA-DR expression in dendritic cells from normal volunteers is CXCR3-dependent.

The antibodies used to measure costimulatory markers were all commercially available and were purchased from BD Biosciences and R&D Systems. From BD Biosciences: CD80 R-phycoerythrin (r-PE)-conjugated mouse anti-human monoclonal antibody (CD80 r-PE, cat.no. 557227), CD40 and CD86 fluorescein isothiocyanate (FITC)-conjugated mouse anti-human monoclonal antibodies (CD40 FITC, cat.no. 555588; CD86 FITC, cat.no 555657), HLA-DR PE-cy5-conjugated mouse anti-human monoclonal antibody (HLA-DR-cy5, cat.no. 555813). From R&D Systems: allophycocyanin-conjugated mouse monoclonal anti-human CXCR3 (CXCR3 APC, cat.no FAB160A). The antibodies used for blocking studies were: monoclonal anti-human CXCR3 antibody (cat.no.MAB160) and mouse IgG1 isotype control (cat.no.MAB002).

EXAMPLE 5

Figure 10B:
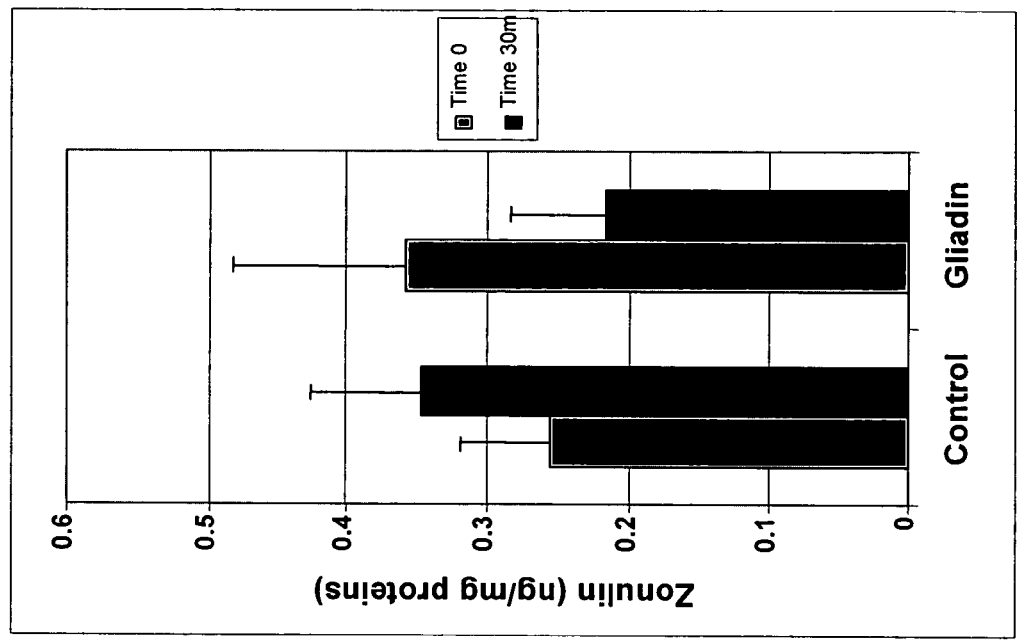
FIG. 10A shows the TEER measurements made in snapwells and FIG. 10B shows the zonulin concentrations.
Figure 10A:
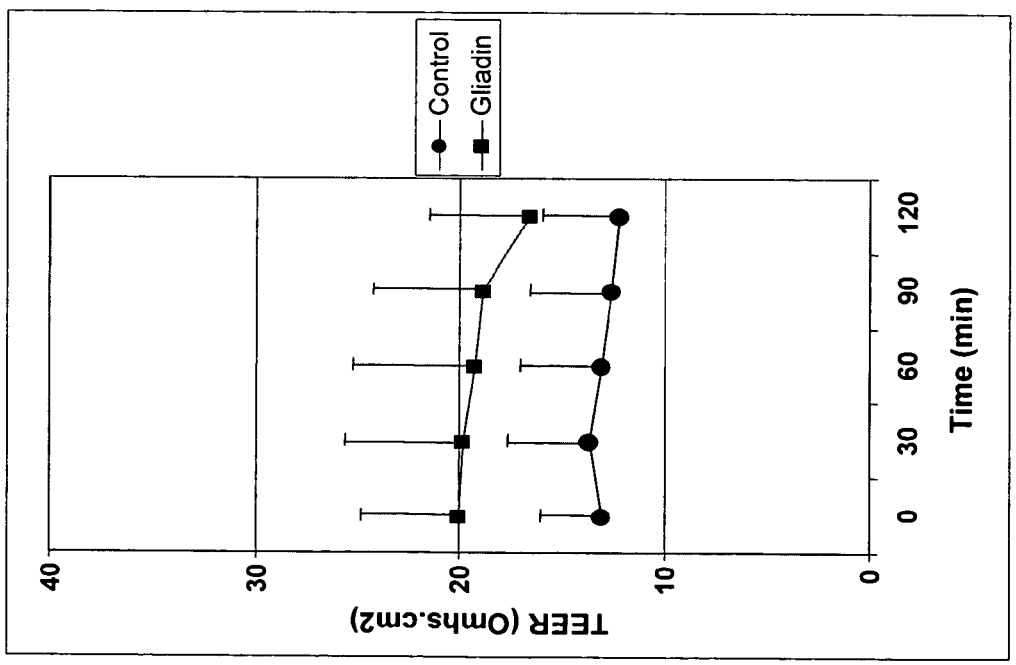

Ex vivo experiments to measure zonulin release and intestinal transepithelial electrical resistance (TEER) changes in response to gliadin exposure were performed using mouse small intestine mounted in microsnapwell chambers. The ex vivo experiments were conducted on both CXCR3 knock out (KO) and C57BL/6 wild-type (WT) mouse intestinal tissues mounted in microsnapwells. When exposed to PT-gliadin, intestinal segments obtained from WT mice (n=10) released zonulin (0.33±0.06 vs. 0.61±0.13 ng/mg protein, baseline vs. post-gliadin exposure, respectively; p<0.04, see FIG. 9B) and showed a significant TEER decrement (24.1±4.5 $\Omega/cm^2$ vs. 14.7±3.2 baseline vs. post-gliadin exposure, respectively; p<0.02, see FIG. 9A). Conversely, intestinal segments obtained from CXCR3 KO mice (n=18) exposed to PT-gliadin failed to release zonulin (0.56±0.15 vs. 0.45±0.13 ng/mg protein, baseline vs. post-gliadin exposure, respectively; p=N.S., see FIG. 10B) and showed no TEER changes (20.0±4.8 $\Omega/cm^2$ vs. 16.5±4.9, baseline vs. post-gliadin exposure, respectively; p N.S., see FIG. 10A).

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims. All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

---

What is claimed is:

1. A method for identifying a gliadin, or fragment of gliadin, which binds the Chemokine (C-X-C motif) receptor 3, comprising:

contacting a gliadin, or fragment of gliadin, comprising at least six amino acid residues with a Chemokine (C-X-C) motif receptor 3; and determining binding of the gliadin or fragment of gliadin to the Chemokine (C-X-C motif) receptor 3 using fluorescence activated cell sorting, fluorescent microscopy, fluorescent spectrophotometry, 2-hybrid transactivation, fluorescent polarization, nuclear magnetic resonance, fluorescent energy transfer or transcriptional activation.

2. The method of claim 1 wherein the fragment comprises at least seven amino acids.

3. The method of claim 1 wherein the fragment comprises at least eight amino acids.

4. The method of claim 1 wherein the fragment comprises at least nine amino acids.

5. The method of claim 1 wherein the fragment comprises at least ten amino acids.

6. The method of claim 1 wherein the fragment is synthesized.

7. The method of claim 1 wherein the fragment is a proteolytic product.

8. A method for identifying a gliadin, or fragment of gliadin, which modulates a Chemokine (C-X-C motif) receptor 3 cell signaling event, comprising:

contacting a gliadin, or fragment of gliadin comprising at least six amino acid residues, with a first cell which expresses Chemokine (C-X-C motif) receptor 3 and with a second cell which does not express Chemokine (C-X-C motif) receptor 3; and comparing the amount of the cell signaling event between the two cell types using a trans epithelial electrical resistance assay, a zonulin release assay, a microglia recruitment assay, a tyrosine kinase phosphorylation assay, a trysosine kinase chemotaxis assay, a MMP-2 gelatinolytic activity assay, or a MMP-9 gelatinolytic activity assay.

9. The method of claim 8 wherein the fragment comprises at least seven amino acid residues.

10. The method of claim 8 wherein the fragment comprises at least eight amino acid residues.

11. The method of claim 8 wherein the fragment comprises at least nine amino acid residues.

12. The method of claim 8 wherein the fragment comprises at least ten amino acid residues.

13. The method of claim 8 wherein the fragment is synthesized.

14. The method of claim 8 wherein the fragment is a proteolytic product.

15. The method of claim 1 wherein the step of determining binding of the gliadin, or fragment of gliadin, to the Chemokine (C-X-C motif) receptor 3 comprises a cell-based assay or a cell-free assay using an isolated Chemokine (C-X-C motif) receptor 3.

16. The method of claim 15 wherein the assay comprises a labeled protein-ligand binding assay, co-immunoprecipitation, immunoassay, or Enzyme-Linked Immunosorbent Assay.

17. The method of claim 1 or claim 8 wherein the gliadin, or fragment of gliadin, comprises a polypeptide sequence selected from the group consisting of SEQ ID NOS: 1-19 or 21-23.

* * * * *

SEQUENCE LISTING

<160> NUMBER OF SEQ ID NOS: 23

<210> SEQ ID NO 1
<211> LENGTH: 290
<212> TYPE: PRT
<213> ORGANISM: Triticum aestivum

<400> SEQUENCE: 1

Met Val Arg Val Pro Val Pro Gln Leu Gln Pro Gln Asn Pro Ser Gln
1               5                   10                  15

```
Gln Gln Pro Gln Glu Gln Val Pro Leu Val Gln Gln Gln Phe Pro
            20                  25                  30

Gly Gln Gln Gln Pro Phe Pro Pro Gln Gln Pro Tyr Pro Gln Pro Gln
            35                  40                  45

Pro Phe Pro Ser Gln Gln Pro Tyr Leu Gln Leu Gln Pro Phe Pro Gln
 50                  55                  60

Pro Gln Leu Pro Tyr Pro Gln Pro Gln Leu Pro Tyr Pro Gln Pro Gln
 65                  70                  75                  80

Leu Pro Tyr Pro Gln Pro Gln Pro Phe Arg Pro Gln Gln Pro Tyr Pro
                85                  90                  95

Gln Ser Gln Pro Gln Tyr Ser Gln Pro Gln Gln Pro Ile Ser Gln Gln
            100                 105                 110

Gln Gln Gln Gln Gln Gln Gln Gln Lys Gln Gln Gln Gln Gln
            115                 120                 125

Gln Gln Gln Ile Leu Gln Gln Ile Leu Gln Gln Leu Ile Pro Cys
            130                 135                 140

Arg Asp Val Val Leu Gln Gln His Ser Ile Ala Tyr Gly Ser Ser Gln
145                 150                 155                 160

Val Leu Gln Gln Ser Thr Tyr Gln Leu Val Gln Gln Leu Cys Cys Gln
                165                 170                 175

Gln Leu Trp Gln Ile Pro Glu Gln Ser Arg Cys Gln Ala Ile His Asn
            180                 185                 190

Val Val His Ala Ile Ile Leu His Gln Gln Gln Gln Gln Gln Gln Gln
                195                 200                 205

Gln Gln Gln Gln Pro Leu Ser Gln Val Ser Phe Gln Gln Pro Gln Gln
            210                 215                 220

Gln Tyr Pro Ser Gly Gln Gly Ser Phe Gln Pro Ser Gln Gln Asn Pro
225                 230                 235                 240

Gln Ala Gln Gly Ser Val Gln Pro Gln Gln Leu Pro Gln Phe Glu Glu
                245                 250                 255

Ile Arg Asn Leu Ala Leu Glu Thr Leu Pro Ala Met Cys Asn Val Tyr
            260                 265                 270

Ile Pro Pro Tyr Cys Thr Ile Ala Pro Val Gly Ile Phe Gly Thr Asn
                275                 280                 285

Tyr Arg
    290

<210> SEQ ID NO 2
<211> LENGTH: 286
<212> TYPE: PRT
<213> ORGANISM: Triticum turgidum subsp. durum

<400> SEQUENCE: 2

Met Lys Thr Phe Leu Ile Leu Ala Leu Leu Ala Ile Val Ala Thr Thr
1               5                   10                  15

Ala Thr Thr Ala Val Arg Val Pro Val Pro Gln Leu Gln Arg Gln Asn
            20                  25                  30

Pro Ser Gln Gln Gln Pro Gln Glu Gln Val Pro Leu Val Gln Gln Gln
            35                  40                  45

Gln Phe Leu Gly Gln Gln Gln Pro Phe Pro Gln Gln Pro Tyr Pro
            50                  55                  60

Gln Pro Gln Pro Phe Pro Ser Gln Gln Pro Tyr Leu Gln Leu Gln Pro
 65                  70                  75                  80

Phe Pro Gln Pro Gln Leu Pro Tyr Ser Gln Pro Gln Pro Phe Arg Pro
```

```
                  85                  90                  95
Gln Gln Pro Tyr Pro Gln Pro Gln Pro Arg Tyr Ser Gln Pro Gln Gln
                100                 105                 110

Pro Ile Ser Gln Gln Gln Gln Gln Gln His Gln Gln His Gln Gln His
            115                 120                 125

His Gln Glu Gln Gln Ile Leu Gln Gln Ile Leu Gln Gln Gln Leu Ile
    130                 135                 140

Pro Cys Met Asp Val Val Leu Gln Gln His Asn Ile Ala His Arg Arg
145                 150                 155                 160

Ser Gln Val Leu Gln Gln Ser Thr Tyr Gln Leu Leu Gln Glu Leu Cys
                165                 170                 175

Cys Gln His Leu Trp Gln Ile Pro Glu Gln Ser Gln Cys Gln Ala Ile
            180                 185                 190

His Asn Val Val His Ala Ile Ile Pro His Gln Gln Lys Gln Gln
    195                 200                 205

Gln Gln Pro Ser Ser Gln Phe Ser Phe Gln Gln Pro Leu Gln Gln Tyr
    210                 215                 220

Pro Leu Gly Gln Gly Ser Phe Arg Pro Ser Gln Gln Asn Pro Gln Ala
225                 230                 235                 240

Gln Gly Ser Val Gln Pro Gln Gln Leu Pro Gln Phe Glu Glu Ile Arg
                245                 250                 255

Asn Leu Ala Leu Gln Thr Leu Pro Ala Met Cys Asn Val Tyr Ile Pro
            260                 265                 270

Pro Tyr Cys Thr Ile Ala Pro Phe Gly Ile Phe Gly Thr Asn
    275                 280                 285

<210> SEQ ID NO 3
<211> LENGTH: 286
<212> TYPE: PRT
<213> ORGANISM: Triticum aestivum

<400> SEQUENCE: 3

Met Lys Thr Phe Leu Ile Leu Val Leu Leu Ala Ile Val Ala Thr Thr
1               5                   10                  15

Ala Thr Thr Ala Val Arg Phe Pro Val Pro Gln Leu Gln Pro Gln Asn
                20                  25                  30

Pro Ser Gln Gln Gln Pro Gln Glu Gln Val Pro Leu Val Gln Gln Gln
            35                  40                  45

Gln Phe Leu Gly Gln Gln Gln Pro Phe Pro Pro Gln Gln Pro Tyr Pro
    50                  55                  60

Gln Pro Gln Pro Phe Pro Ser Gln Leu Pro Tyr Leu Gln Leu Gln Pro
65                  70                  75                  80

Phe Pro Gln Pro Gln Leu Pro Tyr Ser Gln Pro Gln Pro Phe Arg Pro
                85                  90                  95

Gln Gln Pro Tyr Pro Gln Pro Gln Pro Gln Tyr Ser Gln Pro Gln Gln
                100                 105                 110

Pro Ile Ser Gln Gln Gln Gln Gln Gln Gln Gln Gln Gln Gln Gln Gln
            115                 120                 125

Gln Gln Gln Gln Gln Ile Leu Gln Gln Ile Leu Gln Gln Gln Leu Ile
    130                 135                 140

Pro Cys Met Asp Val Val Leu Gln Gln His Asn Ile Ala His Gly Arg
145                 150                 155                 160

Ser Gln Val Leu Gln Gln Ser Thr Tyr Gln Leu Leu Gln Glu Leu Cys
                165                 170                 175
```

```
Cys Gln His Leu Trp Gln Ile Pro Glu Gln Ser Gln Cys Gln Ala Ile
            180                 185                 190

His Asn Val Val His Ala Ile Ile Leu His Gln Gln Lys Gln Gln
        195                 200                 205

Gln Gln Pro Ser Ser Gln Val Ser Phe Gln Gln Pro Leu Gln Gln Tyr
    210                 215                 220

Pro Leu Gly Gln Gly Ser Phe Arg Pro Ser Gln Gln Asn Pro Gln Ala
225                 230                 235                 240

Gln Gly Ser Val Gln Pro Gln Gln Leu Pro Gln Phe Glu Glu Ile Arg
            245                 250                 255

Asn Leu Ala Leu Gln Thr Leu Pro Ala Met Cys Asn Val Tyr Ile Pro
            260                 265                 270

Pro Tyr Cys Thr Ile Ala Pro Phe Gly Ile Phe Gly Thr Asn
            275                 280                 285

<210> SEQ ID NO 4
<211> LENGTH: 302
<212> TYPE: PRT
<213> ORGANISM: Triticum aestivum

<400> SEQUENCE: 4

Met Lys Thr Leu Leu Ile Leu Thr Ile Leu Ala Met Ala Thr Thr Ile
1               5                   10                  15

Ala Thr Ala Asn Met Gln Val Asp Pro Ser Gly Gln Val Gln Trp Pro
            20                  25                  30

Gln Gln Gln Pro Phe Pro Gln Pro Gln Gln Pro Phe Cys Gln Gln Pro
        35                  40                  45

Gln Arg Thr Ile Pro Gln Pro His Gln Thr Phe His His Gln Pro Gln
    50                  55                  60

Gln Thr Phe Pro Gln Pro Gln Gln Thr Tyr Pro His Gln Pro Gln Gln
65                  70                  75                  80

Gln Phe Pro Gln Thr Gln Gln Pro Gln Gln Pro Phe Pro Gln Pro Gln
                85                  90                  95

Gln Thr Phe Pro Gln Gln Pro Gln Leu Pro Phe Pro Gln Gln Pro Gln
            100                 105                 110

Gln Pro Phe Pro Gln Pro Gln Gln Pro Gln Gln Pro Phe Pro Gln Ser
        115                 120                 125

Gln Gln Pro Gln Gln Pro Phe Pro Gln Pro Gln Gln Gln Phe Pro Gln
    130                 135                 140

Pro Gln Gln Pro Gln Gln Ser Phe Pro Gln Gln Gln Pro Ala Ile
145                 150                 155                 160

Gln Ser Phe Leu Gln Gln Gln Met Asn Pro Cys Lys Asn Phe Leu Leu
                165                 170                 175

Gln Gln Cys Asn His Val Ser Leu Val Ser Ser Leu Val Ser Ile Ile
            180                 185                 190

Leu Pro Arg Ser Asp Cys Gln Val Met Gln Gln Gln Cys Gln Gln
        195                 200                 205

Leu Ala Gln Ile Pro Gln Gln Leu Gln Cys Ala Ala Ile His Ser Val
    210                 215                 220

Ala His Ser Ile Ile Met Gln Gln Glu Gln Gln Gln Gly Val Pro Ile
225                 230                 235                 240

Leu Arg Pro Leu Phe Gln Leu Ala Gly Leu Gly Ile Ile Gln Pro
                245                 250                 255

Gln Gln Pro Ala Gln Leu Glu Gly Ile Arg Ser Leu Val Leu Lys Thr
            260                 265                 270
```

```
Leu Pro Thr Met Cys Asn Val Tyr Val Pro Pro Asp Cys Ser Thr Ile
        275                 280                 285

Asn Val Pro Tyr Ala Asn Ile Asp Ala Gly Ile Gly Gly Gln
        290                 295                 300

<210> SEQ ID NO 5
<211> LENGTH: 291
<212> TYPE: PRT
<213> ORGANISM: Triticum aestivum

<400> SEQUENCE: 5

Met Lys Thr Leu Leu Ile Leu Thr Ile Leu Ala Met Ala Ile Thr Ile
1               5                   10                  15

Ala Thr Ala Asn Met Gln Ala Asp Pro Ser Gly Gln Val Gln Trp Pro
            20                  25                  30

Gln Gln Gln Pro Phe Leu Gln Pro His Gln Pro Phe Ser Gln Gln Pro
        35                  40                  45

Gln Gln Ile Phe Pro Gln Pro Gln Gln Thr Phe Pro His Gln Pro Gln
    50                  55                  60

Gln Gln Phe Pro Gln Pro Gln Gln Pro Gln Gln Phe Leu Gln Pro
65                  70                  75                  80

Arg Gln Pro Phe Pro Gln Gln Pro Gln Gln Tyr Pro Gln Gln Pro
                85                  90                  95

Gln Gln Pro Phe Pro Gln Thr Gln Gln Pro Gln Gln Pro Phe Pro Gln
            100                 105                 110

Ser Lys Gln Pro Gln Gln Pro Phe Pro Gln Pro Gln Gln Pro Gln Gln
        115                 120                 125

Ser Phe Pro Gln Gln Pro Ser Leu Ile Gln Ser Leu Gln Gln
    130                 135                 140

Gln Leu Asn Pro Cys Lys Asn Phe Leu Leu Gln Gln Cys Lys Pro Val
145                 150                 155                 160

Ser Leu Val Ser Ser Leu Trp Ser Ile Ile Leu Pro Pro Ser Asp Cys
                165                 170                 175

Gln Val Met Arg Gln Gln Cys Cys Gln Gln Leu Ala Gln Ile Pro Gln
            180                 185                 190

Gln Leu Gln Cys Ala Ala Ile His Ser Val Val His Ser Ile Ile Met
        195                 200                 205

Gln Gln Glu Gln Gln Glu Gln Leu Gly Val Gln Ile Leu Val Pro
    210                 215                 220

Leu Ser Gln Gln Gln Gln Val Gly Gln Gly Ile Leu Val Gln Gly Gln
225                 230                 235                 240

Gly Ile Ile Gln Pro Gln Gln Pro Ala Gln Leu Glu Val Ile Arg Ser
                245                 250                 255

Leu Val Leu Gln Thr Leu Pro Thr Met Cys Asn Val Tyr Val Pro Pro
            260                 265                 270

Tyr Cys Ser Thr Ile Arg Ala Pro Phe Ala Ser Ile Val Ala Ser Ile
        275                 280                 285

Gly Gly Gln
    290

<210> SEQ ID NO 6
<211> LENGTH: 244
<212> TYPE: PRT
<213> ORGANISM: Triticum aestivum

<400> SEQUENCE: 6
```

```
Pro Gln Gln Pro Phe Pro Leu Gln Pro Gln Gln Ser Phe Leu Trp Gln
1               5                   10                  15

Ser Gln Gln Pro Phe Leu Gln Gln Pro Gln Gln Pro Ser Pro Gln Pro
            20                  25                  30

Gln Gln Val Val Gln Ile Ile Ser Pro Ala Thr Pro Thr Thr Ile Pro
        35                  40                  45

Ser Ala Gly Lys Pro Thr Ser Ala Pro Phe Pro Gln Gln Gln Gln Gln
50                  55                  60

His Gln Gln Leu Ala Gln Gln Ile Pro Val Val Gln Pro Ser Ile
65                  70                  75                  80

Leu Gln Gln Leu Asn Pro Cys Lys Val Phe Leu Gln Gln Cys Ser
                85                  90                  95

Pro Val Ala Met Pro Gln Arg Leu Ala Arg Ser Gln Met Leu Gln Gln
            100                 105                 110

Ser Ser Cys His Val Met Gln Gln Cys Cys Gln Gln Leu Pro Gln
        115                 120                 125

Ile Pro Gln Gln Ser Arg Tyr Gln Ala Ile Arg Ala Ile Ile Tyr Ser
130                 135                 140

Ile Ile Leu Gln Glu Gln Gln Val Gln Gly Ser Ile Gln Ser Gln
145                 150                 155                 160

Gln Gln Gln Pro Gln Leu Gly Gln Cys Val Ser Gln Pro Gln Gln
                165                 170                 175

Gln Ser Gln Gln Gln Leu Gly Gln Gln Pro Gln Gln Gln Gln Leu Ala
            180                 185                 190

Gln Gly Thr Phe Leu Gln Pro His Gln Ile Ala Gln Leu Glu Val Met
            195                 200                 205

Thr Ser Ile Ala Leu Arg Ile Leu Pro Thr Met Cys Ser Val Asn Val
210                 215                 220

Pro Leu Tyr Arg Thr Thr Thr Ser Val Pro Phe Gly Val Gly Thr Gly
225                 230                 235                 240

Val Gly Ala Tyr

<210> SEQ ID NO 7
<211> LENGTH: 327
<212> TYPE: PRT
<213> ORGANISM: Triticum aestivum

<400> SEQUENCE: 7

Met Lys Thr Leu Leu Ile Leu Thr Ile Leu Ala Met Ala Ile Thr Ile
1               5                   10                  15

Gly Thr Ala Asn Ile Gln Val Asp Pro Ser Gly Gln Val Gln Trp Leu
            20                  25                  30

Gln Gln Gln Leu Val Pro Gln Leu Gln Gln Pro Leu Ser Gln Gln Pro
        35                  40                  45

Gln Gln Thr Phe Pro Gln Pro Gln Gln Thr Phe Pro His Gln Pro Gln
50                  55                  60

Gln Gln Val Pro Gln Pro Gln Gln Pro Gln Gln Pro Phe Leu Gln Pro
65                  70                  75                  80

Gln Gln Pro Phe Pro Gln Gln Pro Gln Gln Pro Phe Pro Gln Thr Gln
                85                  90                  95

Gln Pro Gln Gln Pro Phe Pro Gln Gln Pro Gln Gln Pro Phe Pro Gln
            100                 105                 110

Thr Gln Gln Pro Gln Gln Pro Phe Pro Gln Gln Pro Gln Gln Pro Phe
        115                 120                 125
```

-continued

```
Pro Gln Thr Gln Gln Pro Gln Gln Pro Phe Pro Gln Leu Gln Gln Pro
        130                 135                 140
Gln Gln Pro Phe Pro Gln Pro Gln Gln Leu Pro Gln Pro Gln Gln
145                 150                 155                 160
Pro Gln Gln Ser Phe Pro Gln Gln Arg Pro Phe Ile Gln Pro Ser
                165                 170                 175
Leu Gln Gln Gln Leu Asn Pro Cys Lys Asn Ile Leu Gln Gln Ser
            180                 185                 190
Lys Pro Ala Ser Leu Val Ser Ser Leu Trp Ser Ile Ile Trp Pro Gln
        195                 200                 205
Ser Asp Cys Gln Val Met Arg Gln Gln Cys Cys Gln Gln Leu Ala Gln
        210                 215                 220
Ile Pro Gln Gln Leu Gln Cys Ala Ala Ile His Ser Val Val His Ser
225                 230                 235                 240
Ile Ile Met Gln Gln Gln Gln Gln Gln Gln Gln Gln Gly Ile Asp
            245                 250                 255
Ile Phe Leu Pro Leu Ser Gln His Glu Gln Val Gly Gln Gly Ser Leu
            260                 265                 270
Val Gln Gly Gln Gly Ile Ile Gln Pro Gln Gln Pro Ala Gln Leu Glu
        275                 280                 285
Ala Ile Arg Ser Leu Val Leu Gln Thr Leu Pro Ser Met Cys Asn Val
        290                 295                 300
Tyr Val Pro Pro Glu Cys Ser Ile Met Arg Ala Pro Phe Ala Ser Ile
305                 310                 315                 320
Val Ala Gly Ile Gly Gly Gln
                325

<210> SEQ ID NO 8
<211> LENGTH: 304
<212> TYPE: PRT
<213> ORGANISM: Triticum aestivum

<400> SEQUENCE: 8

Met Lys Thr Phe Leu Val Phe Ala Leu Ile Ala Val Val Ala Thr Ser
1               5                   10                  15
Ala Ile Ala Gln Met Glu Thr Ser Cys Ile Ser Gly Leu Glu Arg Pro
            20                  25                  30
Trp Gln Gln Gln Pro Leu Pro Pro Gln Gln Ser Phe Ser Gln Gln Pro
        35                  40                  45
Pro Phe Ser Gln Gln Gln Gln Pro Leu Pro Gln Gln Pro Ser Phe
    50                  55                  60
Ser Gln Gln Gln Pro Pro Phe Ser Gln Gln Pro Ile Leu Ser Gln
65                  70                  75                  80
Gln Pro Pro Phe Ser Gln Gln Gln Pro Val Leu Pro Gln Gln Ser
                85                  90                  95
Pro Phe Ser Gln Gln Gln Leu Val Leu Pro Pro Gln Gln Gln Gln
            100                 105                 110
Gln Gln Leu Val Gln Gln Ile Pro Ile Val Gln Pro Ser Val Leu
        115                 120                 125
Gln Gln Leu Asn Pro Cys Lys Val Phe Leu Gln Gln Cys Ser Pro
        130                 135                 140
Val Ala Met Pro Gln Arg Leu Ala Arg Ser Gln Met Trp Gln Gln Ser
145                 150                 155                 160
Ser Cys His Val Met Gln Gln Gln Cys Cys Gln Gln Leu Gln Gln Ile
```

```
                       165                 170                 175
Pro Glu Gln Ser Arg Tyr Glu Ala Ile Arg Ala Ile Ile Tyr Ser Ile
                180                 185                 190

Ile Leu Gln Glu Gln Gln Gln Gly Phe Val Gln Pro Gln Gln Gln Gln
            195                 200                 205

Pro Gln Gln Ser Gly Gln Gly Val Ser Gln Ser Gln Gln Gln Ser Gln
        210                 215                 220

Gln Gln Leu Gly Gln Cys Ser Phe Gln Gln Pro Gln Gln Leu Gly
225                 230                 235                 240

Gln Gln Pro Gln Gln Gln Gln Gln Gln Val Leu Gln Gly Thr Phe
                245                 250                 255

Leu Gln Pro His Gln Ile Ala His Leu Glu Ala Val Thr Ser Ile Ala
            260                 265                 270

Leu Arg Thr Leu Pro Thr Met Cys Ser Val Asn Val Pro Leu Tyr Ser
        275                 280                 285

Ala Thr Thr Ser Val Pro Phe Gly Val Gly Thr Gly Val Gly Ala Tyr
    290                 295                 300

<210> SEQ ID NO 9
<211> LENGTH: 251
<212> TYPE: PRT
<213> ORGANISM: Triticum aestivum

<400> SEQUENCE: 9

Met Lys Thr Leu Leu Ile Leu Thr Ile Leu Ala Met Ala Ile Thr Ile
1               5                   10                  15

Gly Thr Ala Asn Met Gln Val Asp Pro Ser Ser Gln Val Gln Trp Pro
                20                  25                  30

Gln Gln Gln Pro Val Pro Gln Pro His Gln Pro Phe Ser Gln Gln Pro
            35                  40                  45

Gln Gln Thr Phe Pro Gln Pro Gln Gln Thr Phe Pro His Gln Pro Gln
        50                  55                  60

Gln Gln Phe Pro Gln Pro Gln Gln Pro Gln Gln Gln Phe Leu Gln Pro
65                  70                  75                  80

Gln Gln Pro Phe Pro Gln Gln Pro Gln Gln Pro Tyr Pro Gln Gln Pro
                85                  90                  95

Gln Gln Pro Phe Pro Gln Thr Gln Gln Pro Gln Gln Leu Phe Pro Gln
            100                 105                 110

Ser Gln Gln Pro Gln Gln Gln Phe Ser Gln Pro Gln Gln Gln Phe Pro
        115                 120                 125

Gln Pro Gln Gln Pro Gln Gln Ser Phe Pro Gln Gln Gln Pro Pro Phe
    130                 135                 140

Ile Gln Pro Ser Leu Gln Gln Gln Val Asn Pro Cys Lys Asn Phe Leu
145                 150                 155                 160

Leu Gln Gln Cys Lys Pro Val Ser Leu Val Ser Ser Leu Trp Ser Met
                165                 170                 175

Ile Trp Pro Gln Ser Asp Cys Gln Val Met Arg Gln Gln Cys Cys Gln
            180                 185                 190

Gln Leu Ala Gln Ile Pro Gln Gln Leu Gln Cys Ala Ala Ile His Thr
        195                 200                 205

Ile Ile His Ser Ile Ile Met Gln Gln Glu Gln Glu Gln Gln
    210                 215                 220

Gly Met His Ile Leu Leu Pro Leu Tyr Gln Gln Gln Val Gly Gln
225                 230                 235                 240
```

```
Gly Thr Leu Val Gln Gly Gln Gly Ile Ile Gln
                245                 250

<210> SEQ ID NO 10
<211> LENGTH: 307
<212> TYPE: PRT
<213> ORGANISM: Triticum aestivum

<400> SEQUENCE: 10

Met Lys Thr Phe Leu Ile Leu Ala Leu Leu Ala Ile Val Ala Thr Thr
1               5                   10                  15

Ala Arg Ile Ala Val Arg Val Pro Val Pro Gln Leu Gln Pro Gln Asn
            20                  25                  30

Pro Ser Gln Gln Gln Pro Gln Glu Gln Val Pro Leu Val Gln Gln Gln
        35                  40                  45

Gln Phe Pro Gly Gln Gln Gln Pro Phe Pro Gln Gln Pro Tyr Pro
    50                  55                  60

Gln Pro Gln Pro Phe Pro Ser Gln Gln Pro Tyr Leu Gln Leu Gln Pro
65                  70                  75                  80

Phe Pro Gln Pro Gln Leu Pro Tyr Pro Gln Pro Gln Leu Pro Tyr Pro
                85                  90                  95

Gln Pro Gln Leu Pro Tyr Pro Gln Pro Gln Phe Arg Pro Gln Gln
            100                 105                 110

Pro Tyr Pro Gln Ser Pro Gln Tyr Ser Gln Pro Gln Gln Pro Ile
            115                 120                 125

Ser Gln Gln Gln Gln Gln Gln Gln Gln Gln Gln Lys Gln Gln
    130                 135                 140

Gln Gln Gln Gln Gln Gln Ile Leu Gln Gln Ile Leu Gln Gln Gln Leu
145                 150                 155                 160

Ile Pro Cys Arg Asp Val Val Leu Gln Gln His Ser Ile Ala Tyr Gly
                165                 170                 175

Ser Ser Gln Val Leu Gln Gln Ser Thr Tyr Gln Leu Val Gln Gln Leu
            180                 185                 190

Cys Cys Gln Gln Leu Trp Gln Ile Pro Glu Gln Ser Arg Cys Gln Ala
        195                 200                 205

Ile His Asn Val Val His Ala Ile Ile Leu His Gln Gln Gln Gln Gln
    210                 215                 220

Gln Gln Gln Gln Gln Gln Pro Leu Ser Gln Val Ser Phe Gln Gln
225                 230                 235                 240

Pro Gln Gln Gln Tyr Pro Ser Gly Gln Gly Ser Phe Gln Pro Ser Gln
                245                 250                 255

Gln Asn Pro Gln Ala Gln Gly Ser Val Gln Pro Gln Gln Leu Pro Gln
            260                 265                 270

Phe Glu Glu Ile Arg Asn Leu Ala Leu Glu Thr Leu Pro Ala Met Cys
        275                 280                 285

Asn Val Tyr Ile Pro Pro Tyr Cys Thr Ile Ala Pro Val Gly Ile Phe
    290                 295                 300

Gly Thr Asn
305

<210> SEQ ID NO 11
<211> LENGTH: 186
<212> TYPE: PRT
<213> ORGANISM: Triticum aestivum

<400> SEQUENCE: 11
```

```
Pro Gln Pro Gln Pro Gln Tyr Ser Gln Pro Gln Gln Pro Ile Ser Gln
1               5                   10                  15

Gln Gln Gln Gln Gln Gln Gln Gln Gln Gln Gln Gln Gln Gln Glu Gln
            20                  25                  30

Gln Ile Leu Gln Gln Ile Leu Gln Gln Leu Ile Pro Cys Met Asp
        35                  40                  45

Val Val Leu Gln Gln His Asn Ile Ala His Gly Arg Ser Gln Val Leu
    50                  55                  60

Gln Gln Ser Thr Tyr Gln Leu Leu Gln Glu Leu Cys Cys Gln His Leu
65                  70                  75                  80

Trp Gln Ile Pro Glu Gln Ser Gln Cys Gln Ala Ile His Asn Val Val
            85                  90                  95

His Ala Ile Ile Leu His Gln Gln Gln Lys Gln Gln Gln Gln Pro
            100                 105                 110

Ser Ser Gln Phe Ser Phe Gln Gln Pro Leu Gln Gln Tyr Pro Leu Gly
            115                 120                 125

Gln Gly Ser Phe Arg Pro Ser Gln Gln Asn Pro Gln Ala Gln Gly Ser
            130                 135                 140

Val Gln Pro Gln Gln Leu Pro Gln Phe Glu Ile Arg Asn Leu Ala Leu
145                 150                 155                 160

Gln Thr Leu Pro Ala Met Cys Asn Val Tyr Ile Pro Pro Tyr Cys Thr
                165                 170                 175

Ile Ala Pro Phe Gly Ile Phe Gly Thr Asn
            180                 185

<210> SEQ ID NO 12
<211> LENGTH: 313
<212> TYPE: PRT
<213> ORGANISM: Triticum aestivum

<400> SEQUENCE: 12

Met Lys Thr Phe Leu Ile Leu Ala Leu Val Ala Thr Thr Ala Thr Thr
1               5                   10                  15

Ala Val Arg Val Pro Val Pro Gln Leu Gln Pro Lys Asn Pro Ser Gln
            20                  25                  30

Gln Gln Pro Gln Glu Gln Val Pro Leu Val Gln Gln Gln Phe Pro
            35                  40                  45

Gly Gln Gln Gln Gln Phe Pro Pro Gln Gln Pro Tyr Pro Gln Pro Gln
    50                  55                  60

Pro Phe Pro Ser Gln Gln Pro Tyr Leu Gln Leu Gln Pro Phe Pro Gln
65                  70                  75                  80

Pro Gln Pro Phe Leu Pro Gln Leu Pro Tyr Pro Gln Pro Gln Ser Phe
            85                  90                  95

Pro Pro Gln Gln Pro Tyr Pro Gln Gln Arg Pro Lys Tyr Leu Gln Pro
            100                 105                 110

Gln Gln Pro Ile Ser Gln Gln Gln Ala Gln Gln Gln Gln Gln Gln Gln
            115                 120                 125

Gln Gln Gln Gln Gln Gln Gln Gln Gln Ile Leu Gln Gln Ile Leu
            130                 135                 140

Gln Gln Gln Leu Ile Pro Cys Arg Asp Val Val Leu Gln Gln His Asn
145                 150                 155                 160

Ile Ala His Ala Ser Ser Gln Val Leu Gln Gln Ser Thr Tyr Gln Leu
                165                 170                 175

Leu Gln Gln Leu Cys Cys Gln Gln Leu Leu Gln Ile Pro Glu Gln Ser
            180                 185                 190
```

```
Arg Cys Gln Ala Ile His Asn Val His Ala Ile Ile Met His Gln
        195                 200                 205
Gln Glu Gln Gln Gln Gln Leu Gln Gln Gln Gln Gln Gln Leu Gln
    210                 215                 220
Gln Gln Gln Gln Gln Gln Gln Gln Gln Pro Ser Ser Gln Val
225                 230                 235                 240
Ser Phe Gln Gln Pro Gln Gln Tyr Pro Ser Ser Gln Gly Ser Phe
                245                 250                 255
Gln Pro Ser Gln Gln Asn Pro Gln Ala Gln Gly Ser Val Gln Pro Gln
            260                 265                 270
Gln Leu Pro Gln Phe Ala Glu Ile Arg Asn Leu Ala Leu Gln Thr Leu
    275                 280                 285
Pro Ala Met Cys Asn Val Tyr Ile Pro Pro His Cys Ser Thr Thr Ile
290                 295                 300
Ala Pro Phe Gly Ile Phe Gly Thr Asn
305                 310

<210> SEQ ID NO 13
<211> LENGTH: 296
<212> TYPE: PRT
<213> ORGANISM: Triticum aestivum

<400> SEQUENCE: 13

Met Lys Thr Phe Leu Ile Leu Ala Leu Leu Ala Ile Val Ala Thr Thr
1               5                   10                  15
Ala Thr Thr Ala Val Arg Val Pro Val Pro Gln Pro Gln Pro Gln Asn
            20                  25                  30
Pro Ser Gln Pro Gln Pro Gln Gly Gln Val Pro Leu Val Gln Gln Gln
        35                  40                  45
Gln Phe Pro Gly Gln Gln Gln Gln Phe Pro Pro Gln Gln Pro Tyr Pro
    50                  55                  60
Gln Pro Gln Pro Phe Pro Ser Gln Gln Pro Tyr Leu Gln Leu Gln Pro
65                  70                  75                  80
Phe Pro Gln Pro Gln Pro Phe Pro Pro Gln Leu Pro Tyr Pro Gln Pro
                85                  90                  95
Pro Pro Phe Ser Pro Gln Gln Pro Tyr Pro Gln Pro Gln Pro Gln Tyr
            100                 105                 110
Pro Gln Pro Gln Gln Pro Ile Ser Gln Gln Gln Ala Gln Gln Gln Gln
        115                 120                 125
Gln Gln Gln Gln Gln Gln Gln Gln Gln Gln Gln Gln Gln Ile Leu
    130                 135                 140
Gln Gln Ile Leu Gln Gln Gln Leu Ile Pro Cys Arg Asp Val Val Leu
145                 150                 155                 160
Gln Gln His Asn Ile Ala His Ala Arg Ser Gln Val Leu Gln Gln Ser
                165                 170                 175
Thr Tyr Gln Pro Leu Gln Gln Leu Cys Cys Gln Gln Leu Trp Gln Ile
            180                 185                 190
Pro Glu Gln Ser Arg Cys Gln Ala Ile His Asn Val His Ala Ile
        195                 200                 205
Ile Leu His Gln Gln Arg Gln Gln Pro Ser Ser Gln Val Ser
    210                 215                 220
Leu Gln Gln Pro Gln Gln Tyr Pro Ser Gly Gln Gly Phe Phe Gln
225                 230                 235                 240
Pro Ser Gln Gln Asn Pro Gln Ala Gln Gly Ser Val Gln Pro Gln Gln
```

```
                245                 250                 255
Leu Pro Gln Phe Glu Glu Ile Arg Asn Leu Ala Leu Gln Thr Leu Pro
            260                 265                 270

Arg Met Cys Asn Val Tyr Ile Pro Pro Tyr Cys Ser Thr Thr Ile Ala
            275                 280                 285

Pro Phe Gly Ile Phe Gly Thr Asn
            290                 295

<210> SEQ ID NO 14
<211> LENGTH: 297
<212> TYPE: PRT
<213> ORGANISM: Triticum aestivum

<400> SEQUENCE: 14

Met Lys Thr Phe Leu Ile Leu Ala Leu Arg Ala Ile Val Ala Thr Thr
1               5                   10                  15

Ala Thr Ile Ala Val Arg Val Pro Val Pro Gln Leu Gln Pro Gln Asn
            20                  25                  30

Pro Ser Gln Gln Gln Pro Gln Lys Gln Val Pro Leu Val Gln Gln Gln
        35                  40                  45

Gln Phe Pro Gly Gln Gln Pro Phe Pro Pro Gln Gln Pro Tyr Pro
    50                  55                  60

Gln Gln Pro Phe Pro Ser Gln Gln Pro Tyr Met Gln Leu Gln Pro
65                  70                  75                  80

Phe Pro Gln Pro Gln Leu Pro Tyr Pro Gln Pro Gln Leu Pro Tyr Pro
                85                  90                  95

Gln Pro Gln Pro Phe Arg Pro Gln Gln Ser Tyr Pro Gln Pro Gln Pro
            100                 105                 110

Gln Tyr Ser Gln Pro Gln Gln Pro Ile Ser Gln Gln Gln Gln Gln Gln
        115                 120                 125

Gln Gln Gln Gln Gln Gln Gln Gln Ile Leu Gln Gln Ile Leu Gln
    130                 135                 140

Gln Gln Leu Ile Pro Cys Arg Asp Val Val Leu Gln Gln His Ser Ile
145                 150                 155                 160

Ala His Gly Ser Ser Gln Val Leu Gln Gln Ser Thr Tyr Gln Leu Val
                165                 170                 175

Gln Gln Phe Cys Cys Gln Gln Leu Trp Gln Ile Pro Glu Gln Ser Arg
            180                 185                 190

Cys Gln Ala Ile His Asn Val Val His Ala Ile Ile Leu His Gln Gln
        195                 200                 205

Gln Gln Gln Gln Gln Gln Gln Gln Gln Gln Gln Gln Pro Leu Ser
    210                 215                 220

Gln Val Cys Phe Gln Gln Ser Gln Gln Gln Tyr Pro Ser Gly Gln Gly
225                 230                 235                 240

Ser Phe Gln Pro Ser Gln Gln Asn Pro Gln Ala Gln Gly Ser Val Gln
                245                 250                 255

Pro Gln Gln Leu Pro Gln Phe Glu Glu Ile Arg Asn Leu Ala Leu Glu
            260                 265                 270

Thr Leu Pro Ala Met Cys Asn Val Tyr Ile Pro Pro Tyr Cys Thr Ile
        275                 280                 285

Ala Pro Val Gly Ile Phe Gly Thr Asn
    290                 295

<210> SEQ ID NO 15
<211> LENGTH: 282
```

<210> SEQ ID NO 15
<211> LENGTH: 283
<212> TYPE: PRT
<213> ORGANISM: Triticum aestivum

<400> SEQUENCE: 15

Met Lys Thr Phe Leu Ile Leu Ala Leu Leu Ala Ile Val Ala Thr Thr
1               5                   10                  15

Ala Thr Ser Ala Val Arg Val Pro Val Pro Gln Leu Gln Pro Gln Asn
                20                  25                  30

Pro Ser Gln Gln Gln Pro Gln Glu Gln Val Pro Leu Met Gln Gln Gln
            35                  40                  45

Gln Gln Phe Pro Gly Gln Gln Glu Gln Phe Pro Pro Gln Gln Pro Tyr
    50                  55                  60

Pro His Gln Gln Pro Phe Pro Ser Gln Pro Tyr Pro Gln Pro Gln
65                  70                  75                  80

Pro Phe Pro Pro Gln Leu Pro Tyr Pro Gln Thr Gln Pro Phe Pro Pro
                85                  90                  95

Gln Gln Pro Tyr Pro Gln Pro Gln Pro Gln Tyr Pro Gln Pro Gln Gln
            100                 105                 110

Pro Ile Ser Gln Gln Gln Ala Gln Gln Gln Gln Gln Gln Gln Gln Thr
        115                 120                 125

Leu Gln Gln Ile Leu Gln Gln Gln Leu Ile Pro Cys Arg Asp Val Val
130                 135                 140

Leu Gln Gln His Asn Ile Ala His Ala Ser Ser Gln Val Leu Gln Gln
145                 150                 155                 160

Ser Ser Tyr Gln Gln Leu Gln Gln Leu Cys Cys Gln Gln Leu Phe Gln
                165                 170                 175

Ile Pro Glu Gln Ser Arg Cys Gln Ala Ile His Asn Val Val His Ala
            180                 185                 190

Ile Ile Leu His His Gln Gln Gln Gln Gln Gln Gln Pro Ser Ser Gln
        195                 200                 205

Val Ser Tyr Gln Gln Pro Gln Glu Gln Tyr Pro Ser Gly Gln Val Ser
    210                 215                 220

Phe Gln Ser Ser Gln Gln Asn Pro Gln Ala Gln Gly Ser Val Gln Pro
225                 230                 235                 240

Gln Gln Leu Pro Gln Phe Gln Glu Ile Arg Asn Leu Ala Leu Gln Thr
                245                 250                 255

Leu Pro Ala Met Cys Asn Val Tyr Ile Pro Pro Tyr Cys Ser Thr Thr
            260                 265                 270

Ile Ala Pro Phe Gly Ile Phe Gly Thr Asn
        275                 280

<210> SEQ ID NO 16
<211> LENGTH: 291
<212> TYPE: PRT
<213> ORGANISM: Triticum aestivum

<400> SEQUENCE: 16

Met Lys Thr Phe Pro Ile Leu Ala Leu Leu Ala Ile Val Ala Thr Thr
1               5                   10                  15

Ala Thr Thr Ala Val Arg Val Pro Val Pro Gln Leu Gln Leu Gln Asn
                20                  25                  30

Pro Ser Gln Gln Gln Pro Gln Glu Gln Val Pro Leu Val Gln Glu Gln
            35                  40                  45

Gln Phe Gln Gly Gln Gln Gln Pro Phe Pro Pro Gln Gln Pro Tyr Pro
    50                  55                  60

-continued

```
Gln Pro Gln Pro Phe Pro Ser Gln Gln Pro Tyr Leu Gln Leu Gln Pro
 65                  70                  75                  80

Phe Pro Gln Pro Gln Leu Pro Tyr Pro Gln Pro Gln Pro Phe Arg Pro
                 85                  90                  95

Gln Gln Pro Tyr Pro Gln Pro Gln Pro Gln Tyr Ser Gln Pro Gln Gln
            100                 105                 110

Pro Ile Ser Gln Gln Gln Gln Gln Gln Gln Gln Gln Gln Gln Gln Gln
        115                 120                 125

Gln Gln Ile Leu Gln Gln Ile Leu Gln Gln Leu Ile Pro Cys Arg
    130                 135                 140

Asp Val Val Leu Gln Gln His Asn Ile Ala His Gly Ser Ser Gln Val
145                 150                 155                 160

Leu Gln Glu Ser Thr Tyr Gln Leu Val Gln Gln Leu Cys Cys Gln Gln
                165                 170                 175

Leu Trp Gln Ile Pro Glu Gln Ser Arg Cys Gln Ala Ile His Asn Val
                180                 185                 190

Val His Ala Ile Ile Leu His Gln Gln His His His Gln Gln Gln
            195                 200                 205

Gln Gln Gln Gln Gln Gln Pro Leu Ser Gln Val Ser Phe Gln Gln
    210                 215                 220

Pro Gln Gln Gln Tyr Pro Ser Gly Gln Gly Phe Phe Gln Pro Ser Gln
225                 230                 235                 240

Gln Asn Pro Gln Ala Gln Gly Ser Phe Gln Pro Gln Leu Pro Gln
                245                 250                 255

Phe Glu Glu Ile Arg Asn Leu Ala Leu Gln Thr Leu Pro Ala Met Cys
                260                 265                 270

Asn Val Tyr Ile Pro Pro Tyr Cys Thr Ile Ala Pro Phe Gly Ile Phe
            275                 280                 285

Gly Thr Asn
    290

<210> SEQ ID NO 17
<211> LENGTH: 262
<212> TYPE: PRT
<213> ORGANISM: Triticum aestivum

<400> SEQUENCE: 17

Met Lys Thr Phe Leu Ile Leu Ala Leu Leu Ala Ile Val Ala Thr Thr
  1               5                  10                  15

Ala Thr Thr Ala Val Arg Val Pro Val Pro Gln Leu Gln Pro Gln Asn
                 20                  25                  30

Pro Ser Gln Gln Gln Pro Gln Glu Gln Val Pro Leu Val Gln Gln Gln
            35                  40                  45

Gln Phe Leu Gly Gln Gln Pro Phe Pro Gln Gln Pro Tyr Pro
     50                  55                  60

Gln Pro Gln Pro Phe Pro Ser Gln Gln Pro Tyr Leu Gln Leu Gln Pro
 65                  70                  75                  80

Phe Leu Gln Pro Gln Leu Pro Tyr Ser Gln Pro Gln Pro Phe Arg Pro
                 85                  90                  95

Gln Gln Pro Tyr Pro Gln Pro Gln Pro Gln Tyr Ser Gln Pro Gln Gln
            100                 105                 110

Pro Ile Ser Gln Gln Gln Gln Gln Gln Gln Gln Gln Gln Gln Gln Gln
        115                 120                 125

Gln Gln Gln Gln Gln Ile Ile Gln Gln Ile Leu Gln Gln Leu
    130                 135                 140
```

```
Ile Pro Cys Met Asp Val Val Leu Gln Gln His Asn Ile Val His Gly
145                 150                 155                 160

Lys Ser Gln Val Leu Gln Gln Ser Thr Tyr Gln Leu Leu Gln Glu Leu
                165                 170                 175

Cys Cys Gln His Leu Trp Gln Ile Pro Glu Gln Ser Gln Cys Gln Ala
                180                 185                 190

Ile His Asn Val Val His Ala Ile Ile Leu His Gln Gln Gln Lys Gln
                195                 200                 205

Gln Gln Gln Pro Ser Ser Gln Val Ser Phe Gln Gln Pro Leu Gln Gln
            210                 215                 220

Tyr Pro Leu Gly Gln Gly Ser Phe Arg Pro Ser Gln Gln Asn Pro Gln
225                 230                 235                 240

Ala Gln Gly Ser Val Gln Pro Gln Gln Leu Pro Gln Phe Glu Glu Ile
                245                 250                 255

Arg Asn Leu Ala Arg Lys
            260

<210> SEQ ID NO 18
<211> LENGTH: 282
<212> TYPE: PRT
<213> ORGANISM: Triticumaestivum

<400> SEQUENCE: 18

Met Asn Ile Gln Val Asp Pro Ser Ser Gln Val Pro Trp Pro Gln Gln
1               5                   10                  15

Gln Pro Phe Pro Gln Pro His Gln Pro Phe Ser Gln Gln Pro Gln Gln
                20                  25                  30

Thr Phe Pro Gln Pro Gln Gln Thr Phe Pro His Gln Pro Gln Gln Gln
            35                  40                  45

Phe Ser Gln Pro Gln Gln Pro Gln Gln Phe Ile Gln Pro Gln Gln
    50                  55                  60

Pro Phe Pro Gln Gln Pro Gln Gln Thr Tyr Pro Gln Arg Pro Gln Gln
65                  70                  75                  80

Pro Phe Pro Gln Thr Gln Gln Pro Gln Gln Pro Phe Pro Gln Ser Gln
                85                  90                  95

Gln Pro Gln Gln Pro Phe Pro Gln Pro Gln Gln Gln Phe Pro Gln Pro
                100                 105                 110

Gln Gln Pro Gln Gln Ser Phe Pro Gln Gln Gln Pro Ser Leu Ile Gln
            115                 120                 125

Gln Ser Leu Gln Gln Gln Leu Asn Pro Cys Lys Asn Phe Leu Leu Gln
130                 135                 140

Gln Cys Lys Pro Val Ser Leu Val Ser Ser Leu Trp Ser Met Ile Leu
145                 150                 155                 160

Pro Arg Ser Asp Cys Gln Val Met Arg Gln Gln Cys Cys Gln Gln Leu
                165                 170                 175

Ala Gln Ile Pro Gln Gln Leu Gln Cys Ala Ala Ile His Ser Ile Val
                180                 185                 190

His Ser Ile Ile Met Gln Gln Glu Gln Gln Gln Arg Gln Gly Val
            195                 200                 205

Gln Ile Leu Val Pro Leu Ser Gln Gln Gln Gln Val Gly Gln Gly Thr
            210                 215                 220

Leu Val Gln Gly Gln Gly Ile Ile Gln Pro Gln Gln Pro Ala Gln Leu
225                 230                 235                 240

Glu Val Ile Arg Ser Leu Val Leu Gln Thr Leu Ala Thr Met Cys Asn
```

```
                    245                 250                 255
Val Tyr Val Pro Pro Tyr Cys Ser Thr Ile Arg Ala Pro Phe Ala Ser
                260                 265                 270

Ile Val Ala Gly Ile Gly Gly Gln Tyr Arg
            275                 280

<210> SEQ ID NO 19
<211> LENGTH: 28
<212> TYPE: PRT
<213> ORGANISM: Triticum monococcum

<400> SEQUENCE: 19

Ala Arg Gln Leu Asn Pro Ser Asp Gln Glu Leu Gln Ser Pro Gln Gln
1               5                   10                  15

Leu Tyr Pro Gln Gln Pro Tyr Pro Gln Gln Pro Tyr
            20                  25

<210> SEQ ID NO 20
<211> LENGTH: 13
<212> TYPE: PRT
<213> ORGANISM: Triticum aestivum

<400> SEQUENCE: 20

Leu Gly Gln Gln Gln Pro Phe Pro Pro Gln Gln Pro Tyr
1               5                   10

<210> SEQ ID NO 21
<211> LENGTH: 801
<212> TYPE: PRT
<213> ORGANISM: Mus musculus

<400> SEQUENCE: 21

Met Ala Ser Gly Ala Asp Ser Lys Gly Asp Asp Leu Ser Thr Ala Ile
1               5                   10                  15

Leu Lys Gln Lys Asn Arg Pro Asn Arg Leu Ile Val Asp Glu Ala Ile
            20                  25                  30

Asn Glu Asp Asn Ser Val Val Ser Leu Ser Gln Pro Lys Met Asp Glu
        35                  40                  45

Leu Gln Leu Phe Arg Gly Asp Thr Val Leu Leu Lys Gly Lys Lys Arg
    50                  55                  60

Arg Glu Ala Val Cys Ile Val Leu Ser Asp Asp Thr Cys Ser Asp Glu
65                  70                  75                  80

Lys Ile Arg Met Asn Arg Val Val Arg Asn Asn Leu Arg Val Arg Leu
                85                  90                  95

Gly Asp Val Ile Ser Ile Gln Pro Cys Pro Asp Val Lys Tyr Gly Lys
            100                 105                 110

Arg Ile His Val Leu Pro Ile Asp Asp Thr Val Glu Gly Ile Thr Gly
        115                 120                 125

Asn Leu Phe Glu Val Tyr Leu Lys Pro Tyr Phe Leu Glu Ala Tyr Arg
    130                 135                 140

Pro Ile Arg Lys Gly Asp Ile Phe Leu Val Arg Gly Gly Met Arg Ala
145                 150                 155                 160

Val Glu Phe Lys Val Val Glu Thr Asp Pro Ser Pro Tyr Cys Ile Val
                165                 170                 175

Ala Pro Asp Thr Val Ile His Cys Glu Gly Glu Pro Ile Lys Arg Glu
            180                 185                 190

Asp Glu Glu Glu Ser Leu Asn Glu Val Gly Tyr Asp Asp Ile Gly Gly
        195                 200                 205
```

-continued

```
Cys Arg Lys Gln Leu Ala Gln Ile Lys Glu Met Val Glu Leu Pro Leu
    210                 215                 220

Arg His Pro Ala Leu Phe Lys Ala Ile Gly Val Lys Pro Pro Arg Gly
225                 230                 235                 240

Ile Leu Leu Tyr Gly Pro Pro Gly Thr Gly Lys Thr Leu Ile Ala Arg
                245                 250                 255

Ala Val Ala Asn Glu Thr Gly Ala Phe Phe Leu Ile Asn Gly Pro
            260                 265                 270

Glu Ile Met Ser Lys Leu Ala Gly Glu Ser Glu Ser Asn Leu Arg Lys
        275                 280                 285

Ala Phe Glu Glu Ala Glu Lys Asn Ala Pro Ala Ile Ile Phe Ile Asp
    290                 295                 300

Glu Leu Asp Ala Ile Ala Pro Lys Arg Glu Lys Thr His Gly Glu Val
305                 310                 315                 320

Glu Arg Arg Ile Val Ser Gln Leu Leu Thr Leu Met Asp Gly Leu Lys
                325                 330                 335

Gln Arg Ala His Val Ile Val Met Ala Ala Thr Asn Arg Pro Asn Ser
            340                 345                 350

Ile Asp Pro Ala Leu Arg Arg Phe Gly Arg Phe Asp Arg Glu Val Asp
        355                 360                 365

Ile Gly Ile Pro Asp Ala Thr Gly Arg Leu Glu Ile Leu Gln Ile His
    370                 375                 380

Thr Lys Asn Met Lys Leu Ala Asp Asp Val Asp Leu Glu Gln Val Ala
385                 390                 395                 400

Asn Glu Thr His Gly His Val Gly Ala Asp Leu Ala Ala Leu Cys Ser
                405                 410                 415

Glu Ala Ala Leu Gln Ala Ile Arg Lys Lys Met Asp Leu Ile Asp Leu
            420                 425                 430

Glu Asp Glu Thr Ile Asp Ala Glu Val Met Asn Ser Leu Ala Val Thr
        435                 440                 445

Met Asp Asp Phe Arg Trp Ala Leu Ser Gln Ser Asn Pro Ser Ala Leu
    450                 455                 460

Arg Glu Thr Val Val Glu Val Pro Gln Val Thr Trp Glu Asp Ile Gly
465                 470                 475                 480

Gly Leu Glu Asp Val Lys Arg Glu Leu Gln Glu Leu Val Gln Tyr Pro
                485                 490                 495

Val Glu His Pro Asp Lys Phe Leu Lys Phe Gly Met Thr Pro Ser Lys
            500                 505                 510

Gly Val Leu Phe Tyr Gly Pro Pro Gly Cys Gly Lys Thr Leu Leu Ala
        515                 520                 525

Lys Ala Ile Ala Asn Glu Cys Gln Ala Asn Phe Ile Ser Ile Lys Gly
    530                 535                 540

Pro Glu Leu Leu Thr Met Trp Phe Gly Glu Ser Glu Ala Asn Val Arg
545                 550                 555                 560

Glu Ile Phe Asp Lys Ala Arg Val Leu Phe Phe Asp Glu Leu Asp Ser
                565                 570                 575

Ile Ala Lys Ala Arg Gly Gly Asn Ile Gly Asp Gly Gly Gly Ala Ala
            580                 585                 590

Asp Arg Val Ile Asn Gln Ile Leu Thr Glu Met Asp Gly Met Ser Thr
        595                 600                 605

Lys Lys Asn Val Phe Ile Ile Gly Ala Thr Asn Arg Pro Asp Ile Ile
    610                 615                 620
```

```
Asp Pro Ala Ile Leu Arg Pro Gly Arg Leu Asp Gln Leu Ile Tyr Ile
625                 630                 635                 640

Pro Leu Pro Asp Glu Lys Ser Arg Val Ala Ile Leu Lys Ala Asn Leu
            645                 650                 655

Arg Lys Ser Pro Val Ala Lys Asp Val Asp Leu Glu Phe Leu Ala Lys
            660                 665                 670

Met Thr Asn Gly Phe Ser Gly Ala Asp Leu Thr Glu Ile Cys Gln Arg
        675                 680                 685

Ala Cys Lys Leu Ala Ile Arg Glu Ser Ile Glu Ser Glu Ile Arg Arg
690                 695                 700

Glu Arg Glu Arg Gln Thr Asn Pro Ser Ala Met Glu Val Glu Glu Asp
705                 710                 715                 720

Asp Pro Val Pro Glu Ile Arg Arg Asp His Phe Glu Glu Ala Met Arg
            725                 730                 735

Phe Ala Arg Arg Ser Val Ser Asp Asn Asp Ile Arg Lys Tyr Glu Met
            740                 745                 750

Phe Ala Gln Thr Leu Gln Gln Ser Arg Gly Phe Gly Ser Phe Arg Phe
        755                 760                 765

Pro Ser Gly Asn Gln Gly Gly Ala Gly Pro Ser Gln Gly Ser Gly Gly
770                 775                 780

Gly Thr Gly Gly Ser Val Tyr Thr Glu Asp Asn Asp Asp Leu Tyr Gly
785                 790                 795                 800

Gly

<210> SEQ ID NO 22
<211> LENGTH: 368
<212> TYPE: PRT
<213> ORGANISM: Homo sapiens

<400> SEQUENCE: 22

Met Val Leu Glu Val Ser Asp His Gln Val Leu Asn Asp Ala Glu Val
1               5                   10                  15

Ala Ala Leu Leu Glu Asn Phe Ser Ser Tyr Asp Tyr Gly Glu Asn
            20                  25                  30

Glu Ser Asp Ser Cys Cys Thr Ser Pro Pro Cys Pro Gln Asp Phe Ser
        35                  40                  45

Leu Asn Phe Asp Arg Ala Phe Leu Pro Ala Leu Tyr Ser Leu Leu Phe
    50                  55                  60

Leu Leu Gly Leu Leu Gly Asn Gly Ala Val Ala Ala Val Leu Leu Ser
65                  70                  75                  80

Arg Arg Thr Ala Leu Ser Ser Thr Asp Thr Phe Leu Leu His Leu Ala
                85                  90                  95

Val Ala Asp Thr Leu Leu Val Leu Thr Leu Pro Leu Trp Ala Val Asp
            100                 105                 110

Ala Ala Val Gln Trp Val Phe Gly Ser Gly Leu Cys Lys Val Ala Gly
        115                 120                 125

Ala Leu Phe Asn Ile Asn Phe Tyr Ala Gly Ala Leu Leu Leu Ala Cys
    130                 135                 140

Ile Ser Phe Asp Arg Tyr Leu Asn Ile Val His Ala Thr Gln Leu Tyr
145                 150                 155                 160

Arg Arg Gly Pro Pro Ala Arg Val Thr Leu Thr Cys Leu Ala Val Trp
                165                 170                 175

Gly Leu Cys Leu Leu Phe Ala Leu Pro Asp Phe Ile Phe Leu Ser Ala
            180                 185                 190
```

```
His His Asp Glu Arg Leu Asn Ala Thr His Cys Gln Tyr Asn Phe Pro
        195                 200                 205

Gln Val Gly Arg Thr Ala Leu Arg Val Leu Gln Leu Val Ala Gly Phe
        210                 215                 220

Leu Leu Pro Leu Leu Val Met Ala Tyr Cys Tyr Ala His Ile Leu Ala
225                 230                 235                 240

Val Leu Leu Val Ser Arg Gly Gln Arg Leu Arg Ala Met Arg Leu
                245                 250                 255

Val Val Val Val Val Ala Phe Ala Leu Cys Trp Thr Pro Tyr His
            260                 265                 270

Leu Val Val Leu Val Asp Ile Leu Met Asp Leu Gly Ala Leu Ala Arg
            275                 280                 285

Asn Cys Gly Arg Glu Ser Arg Val Asp Val Ala Lys Ser Val Thr Ser
        290                 295                 300

Gly Leu Gly Tyr Met His Cys Cys Leu Asn Pro Leu Leu Tyr Ala Phe
305                 310                 315                 320

Val Gly Val Lys Phe Arg Glu Arg Met Trp Met Leu Leu Arg Leu
                325                 330                 335

Gly Cys Pro Asn Gln Arg Gly Leu Gln Arg Gln Pro Ser Ser Ser Arg
                340                 345                 350

Arg Asp Ser Ser Trp Ser Glu Thr Ser Glu Ala Ser Tyr Ser Gly Leu
                355                 360                 365

<210> SEQ ID NO 23
<211> LENGTH: 367
<212> TYPE: PRT
<213> ORGANISM: Mus musculus

<400> SEQUENCE: 23

Met Tyr Leu Glu Val Ser Glu Arg Gln Val Leu Asp Ala Ser Asp Phe
1               5                   10                  15

Ala Phe Leu Leu Glu Asn Ser Thr Ser Pro Tyr Asp Tyr Gly Glu Asn
                20                  25                  30

Glu Ser Asp Phe Ser Asp Ser Pro Pro Cys Pro Gln Asp Phe Ser Leu
            35                  40                  45

Asn Phe Asp Arg Thr Phe Leu Pro Ala Leu Tyr Ser Leu Leu Phe Leu
        50                  55                  60

Leu Gly Leu Leu Gly Asn Gly Ala Val Ala Ala Val Leu Leu Ser Gln
65                  70                  75                  80

Arg Thr Ala Leu Ser Ser Thr Asp Thr Phe Leu Leu His Leu Ala Val
                85                  90                  95

Ala Asp Val Leu Leu Val Leu Thr Leu Pro Leu Trp Ala Val Asp Ala
            100                 105                 110

Ala Val Gln Trp Val Phe Gly Pro Gly Leu Cys Lys Val Ala Gly Ala
        115                 120                 125

Leu Phe Asn Ile Asn Phe Tyr Ala Gly Ala Phe Leu Leu Ala Cys Ile
    130                 135                 140

Ser Phe Asp Arg Tyr Leu Ser Ile Val His Ala Thr Gln Ile Tyr Arg
145                 150                 155                 160

Arg Asp Pro Arg Val Arg Val Ala Leu Thr Cys Ile Val Val Trp Gly
                165                 170                 175

Leu Cys Leu Leu Phe Ala Leu Pro Asp Phe Ile Tyr Leu Ser Ala Asn
            180                 185                 190

Tyr Asp Gln Arg Leu Asn Ala Thr His Cys Gln Tyr Asn Phe Pro Gln
        195                 200                 205
```

```
Val Gly Arg Thr Ala Leu Arg Val Leu Gln Leu Val Ala Gly Phe Leu
    210                 215                 220

Leu Pro Leu Leu Val Met Ala Tyr Cys Tyr Ala His Ile Leu Ala Val
225                 230                 235                 240

Leu Leu Val Ser Arg Gly Gln Arg Arg Phe Arg Ala Met Arg Leu Val
            245                 250                 255

Val Val Val Val Ala Ala Phe Ala Val Cys Trp Thr Pro Tyr His Leu
            260                 265                 270

Val Val Leu Val Asp Ile Leu Met Asp Val Gly Val Leu Ala Arg Asn
            275                 280                 285

Cys Gly Arg Glu Ser His Val Asp Val Ala Lys Ser Val Thr Ser Gly
        290             295                 300

Met Gly Tyr Met His Cys Cys Leu Asn Pro Leu Leu Tyr Ala Phe Val
305                 310                 315                 320

Gly Val Lys Phe Arg Glu Gln Met Trp Met Leu Phe Thr Arg Leu Gly
            325                 330                 335

Arg Ser Asp Gln Arg Gly Pro Gln Arg Gln Pro Ser Ser Ser Arg Arg
            340                 345                 350

Glu Ser Ser Trp Ser Glu Thr Thr Glu Ala Ser Tyr Leu Gly Leu
        355                 360                 365
```